(12) United States Patent
Wendland

(10) Patent No.: US 9,296,668 B2
(45) Date of Patent: *Mar. 29, 2016

(54) POLYMERIZABLE SPIROBISINDANE MONOMERS AND POLYMERS PREPARED THEREFROM

(71) Applicant: 3M INNOVATIVE PROPERTIES COMPANY, St. Paul, MN (US)

(72) Inventor: Michael S. Wendland, North St. Paul, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/430,022

(22) PCT Filed: Sep. 12, 2013

(86) PCT No.: PCT/US2013/059400
§ 371 (c)(1),
(2) Date: Mar. 20, 2015

(87) PCT Pub. No.: WO2014/052021
PCT Pub. Date: Apr. 3, 2014

(65) Prior Publication Data
US 2015/0239806 A1    Aug. 27, 2015

Related U.S. Application Data

(60) Provisional application No. 61/705,358, filed on Sep. 25, 2012.

(51) Int. Cl.
| | | |
|---|---|---|
| *C07C 13/72* | (2006.01) | |
| *C07C 35/44* | (2006.01) | |
| *C07C 49/683* | (2006.01) | |
| *C08F 36/20* | (2006.01) | |
| *C08F 212/34* | (2006.01) | |
| *C08F 212/36* | (2006.01) | |
| *C08F 216/10* | (2006.01) | |
| *C08F 216/36* | (2006.01) | |
| *C08F 4/34* | (2006.01) | |

(52) U.S. Cl.
CPC ............ *C07C 13/72* (2013.01); *C07C 35/44* (2013.01); *C07C 49/683* (2013.01); *C08F 36/20* (2013.01); *C08F 212/34* (2013.01); *C08F 212/36* (2013.01); *C08F 216/10* (2013.01); *C08F 216/36* (2013.01); *C07C 2103/94* (2013.01)

(58) Field of Classification Search
CPC ...... C07C 13/72; C07C 35/44; C07C 49/683; C07C 2103/94; C08F 36/20; C08F 212/34; C08F 212/36
USPC ....................... 526/284; 568/327, 808; 585/27
See application file for complete search history.

(56) References Cited

U.S. PATENT DOCUMENTS

| | | | | |
|---|---|---|---|---|
| 3,945,968 A | * | 3/1976 | Goletto | C08K 5/13 521/116 |
| 6,361,884 B1 | | 3/2002 | Kreuder | |
| 9,139,674 B2 | * | 9/2015 | Wendland | C08F 212/08 |
| 2014/0288232 A1 | | 9/2014 | Grootaert | |

FOREIGN PATENT DOCUMENTS

| | | | |
|---|---|---|---|
| DE | 3434286 | * | 5/1985 |
| DE | 19606511 | | 9/1997 |
| WO | WO 2005/012397 | | 2/2005 |

OTHER PUBLICATIONS

Budd, "Polymers of intrinsic microporosity (PIMs): robust, solution-processable, organic nanoporous materials", Chem. Commun., 2004, pp. 230-231.
Carta, "Novel Spirobisindanes for Use as Precursors to Polymers of Intrinsic Microporosity", Organic Letters, 2008, vol. 10, No. 13, pp. 2641-2643.
Liu, "Unexpected Behavior of 1-Chlorodecane as a Novel Porogen in the Preparation of High-Porosity Poly(divinylbenzene) Microspheres", J. Phys. Chem. C., 2008, vol. 112, pp. 13171-13174.
Liu, "Efficient and stable solid acid catalysts synthesized from sulfonation of swelling mesoporous polydivinylbenzenes", Journal of Catalysis, 2010, vol. 271, pp. 52-58.
Nyhus, "Formation of the Porous Structure During the Polymerization of meta-Divinylbenzene and para-Divinylbenzene with Toluene and 2-Ethylhexanoic Acid (2-EHA) as Porogens", Journal of Polymer Science: Part A: Polymer Chemistry, 1999, vol. 37, pp. 3973-3990.
Podlesnyuk, "Sorption of organic vapours by macroporous and hypercrosslinked polymeric adsorbents", Reactive & Functional Polymers, 1999, vol. 42, pp. 181-191.
Thomas, "Pure- and mixed-gas permeation properties of a microporous spirobisindane-based ladder polymer (PIM-1)", Journal of Membrane Science, 2009, vol. 333, pp. 125-131.
Thomas, "Hydrocarbon/hydrogen mixed-gas permeation properties of PIM-1, an amorphous microporous spirobisindane polymer", Journal of Membrane Science, 2009, vol. 338, pp. 1-4.
Webb, Analytical Methods in Fine Particle Technology, Chapter 3, "Surface Area and Pore Structure by Gas Adsorption", pp. 53-153, Micromeritics Instrument Corpation, Norcross, GA, USA (1997).
Zhang, "Superhydrophobic nanoporous polymers as efficient adsorbents for organic compounds", Nano Today, 2009, vol. 4, pp. 135-142.
Zhao, "Poly(divinylbenzene) Particles of Large Specific Surface Area Prepared by Dispersion Polymerization", Advanced Materials Research, 2011, vols. 148-149, pp. 1281-1285.
International Search Report for PCT International Application No. PCT/US2013/059400, mailed on Oct. 23, 2013, 3 pages.

* cited by examiner

*Primary Examiner* — Fred M Teskin
(74) *Attorney, Agent, or Firm* — Jean A. Lown

(57) ABSTRACT

Monomers and polymerizable compositions that can be polymerized using a free-radical polymerization reaction are provided. The monomers have two vinyl groups as well as a spirobisindane-type structure. Polymers prepared from the polymerizable compositions are also provided. The polymers can be porous.

15 Claims, 4 Drawing Sheets

POLYMERIZABLE SPIROBISINDANE MONOMERS AND POLYMERS PREPARED THEREFROM

CROSS REFERENCE TO RELATED APPLICATIONS

This application is a national stage filing under 35 U.S.C. 371 of PCT/US2013/059400, filed Sep. 12, 2013, which claims priority to U.S. Provisional Application No. 61/705,358, filed Sep. 25, 2012, the disclosures of which are incorporated by reference in its/their entirety herein.

TECHNICAL FIELD

Polymerizable spirobisindane monomers and polymers prepared from these monomers are described.

BACKGROUND

Porous materials can be useful in a variety of different applications. For example, porous materials can be used as sorptive media, as gas separation membranes, as the detection material in various sensors, as catalysts, and as light weight materials. In some applications, porous materials with micropores (i.e., pores less than 2 nanometers) are particularly useful. Many of the state-of-the art microporous materials are made using expensive raw materials, and/or are made using processes that are limited to the preparation of fairly small quantities, and/or are difficult to process into useable forms. Additionally, because of the instability of some of these materials under ambient conditions, the total porosity can deteriorate over time and usage.

Some example microporous materials of interest are polymers with intrinsic microporosity. One example synthesis method for this type of polymeric material is shown in Reaction Scheme A where 5,5',6,6'-tetrahydroxy-3,3,3',3'-tetramethyl-1,1'-spirobisindane is reacted with 2,3,5,6-tetrafluoroterephthalonitrile to form a polymeric material with fused dioxin rings as linking groups. These polymers and their synthesis methods are described more fully, for example, in Budd et al., *Chem, Commun.,* 2004, 230 and in U.S. Pat. No. 7,690,514 (McKeown et al.).

Reaction Scheme A

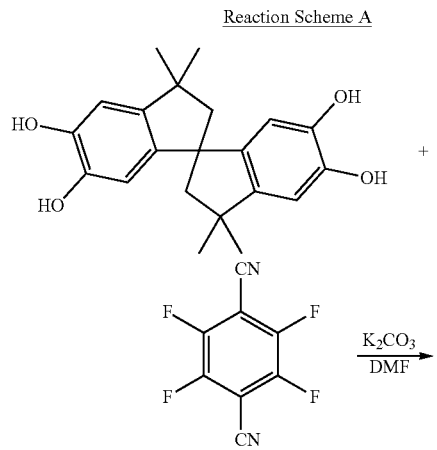

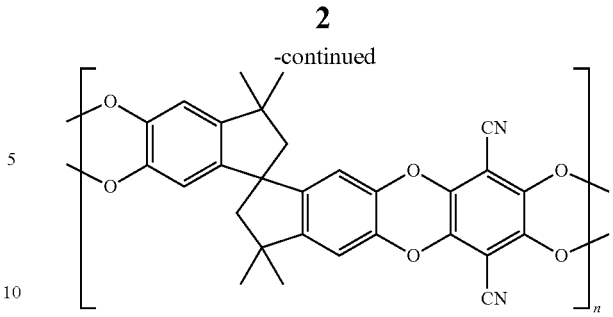

Polymers with intrinsic microporosity are characterized by a rigid backbone containing regular points of contortion. This characteristic of the backbone results in poor packing of the polymeric chains with each other. The interstitial space between the polymer chains tends to result in microporosity. The surface area of these polymers can be greater than 600 $m^2$/gram, greater than 700 $m^2$/gram, or even greater than 800 $m^2$/gram. Unlike many other microporous materials, these polymers are soluble in many common organic solvents and advantageously can be coated from a solution to form a microporous coating. On the other hand, the polymers with intrinsic microporosity typically are not suitable for applications that require large volumes of material. The polymerization times tend to be lengthy (e.g., several days) and the monomers used to form the polymers are often quite expensive.

SUMMARY

Monomers and polymerizable compositions that can be polymerized using a free-radical polymerization reaction are provided. The monomers have two vinyl groups as well as a spirobisindane-type structure. Additionally, polymers and methods of making polymers from the polymerizable compositions are provided. The polymers can be porous.

In a first aspect, a compound of Formula (I) is provided.

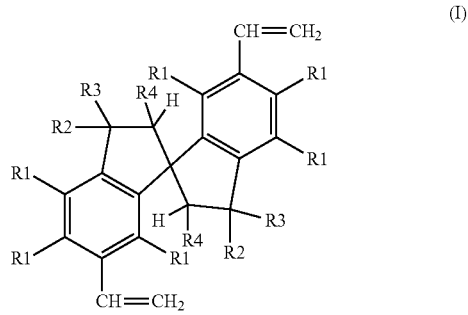

In Formula (I), each R1 is independently hydrogen, halo, alkyl, aryl, alkaryl, or aralkyl. Each R2 is independently hydrogen, alkyl, alkoxy, aryl, alkaryl, aralkyl, hydroxyl, silyloxy, combines with a R3 connected to a same carbon atom to form a cyclic alkyl, combines with a R3 connected to the same carbon atom to form a cyclic alkyl that is fused to one or more carbocyclic rings, or combines with R3 and the carbon atom to which both R2 and R3 are connected to form a carbonyl group. Each R3 is independently hydrogen, alkyl, alkoxy, aryl, alkaryl, aralkyl, hydroxyl, silyloxy, combines with a R2 connected to a same carbon atom to form a cyclic alkyl, combines with a R2 connected to the same carbon atom to form a cyclic alkyl that is fused to one or more carbocyclic rings, combines with R2 and the carbon to which both R2 and R3 are connected to form a carbonyl group, or combines with R4 connected to adjacent carbon atom to form a carbon-carbon bond. Each R4 is independently hydrogen or combines with R3 connected to an adjacent carbon atom to form a carbon-carbon bond.

In a second aspect, a polymerizable composition is provided that contains a compound of Formula (I) as described above.

In a third aspect, a polymer that includes a polymerized reaction product of a polymerizable composition is provided. The polymerizable composition contains a compound of Formula (I) as described above.

DETAILED DESCRIPTION

Figure 1:
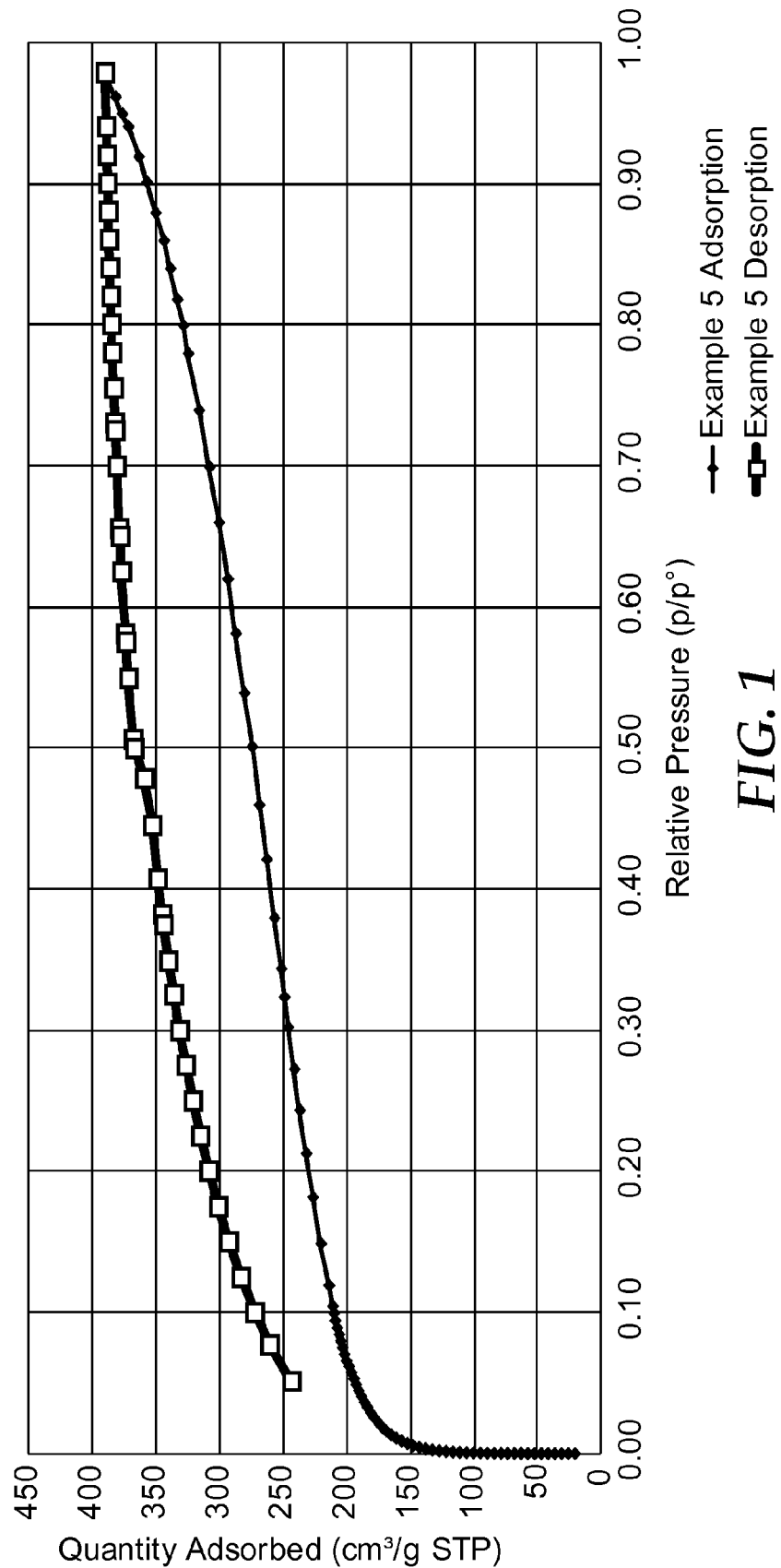
FIG. 1 is the plot of the nitrogen adsorption and desorption isotherm at 77° K for an exemplary porous polymeric material prepared from a monomer of Formula (I).

Monomers having two vinyl groups as well as a spirobisindane-type structure are provided. The monomers can be polymerized using free radical reactions. Polymerizable compositions containing the monomers and polymers prepared from polymerizable compositions containing the monomer are also provided. The polymeric materials prepared using the spirobisindane-type monomers can be porous. Depending on the composition of the polymerizable compositions used to prepare the polymers and the reaction conditions, polymeric materials with micropores, mesopores, or both can be prepared.

The terms "a", "an", and "the" are used interchangeably with "at least one" to mean one or more of the elements being described.

The term "halo" refers to a monovalent group that is a radical of a halogen atom. The halo can be fluoro, chloro, bromo, or iodo.

The term "alkyl" refers to a monovalent group that is a radical of an alkane. The alkyl group can have 1 to 20 carbon atoms. The alkyl group can be linear, branched, cyclic, or a combination thereof. When the alkyl is linear, it can have 1 to 20 carbon atoms. When the alkyl is branched or cyclic, it can have 3 to 20 carbon atoms.

The term "alkoxy" refers to a monovalent group of formula —OR where R is an alkyl as defined above.

The term "aryl" refers to a monovalent group that is a radical of an aromatic carbocyclic compound. The aryl group has at least one aromatic carbocyclic ring and can have 1 to 5 optional rings that are connected to or fused to the aromatic carbocyclic ring. The additional rings can be aromatic, aliphatic, or a combination thereof. The aryl group usually has 5 to 20 carbon atoms.

The term "alkaryl" refers to an aryl group substituted with at least one alkyl group. The alkaryl group contains 6 to 40 carbon atoms. The alkaryl group often contains an aryl group having 5 to 20 carbon atoms and an alkyl group having 1 to 20 carbon atoms.

The term "aralkyl" refers to an alkyl group substituted with at least one aryl group. The aralkyl group contains 6 to 40 carbon atoms. The aralkyl group often contains an alkyl group having 1 to 20 carbon atoms and an aryl group having 5 to 20 carbon atoms.

The term "carbocyclic group" refers to an aliphatic or aromatic carbon ring structure. The carbocyclic group can be saturated, partially unsaturated, or unsaturated. The carbocyclic group often contains 5 to 20 carbon atoms.

The term "silyloxy" refers to a monovalent group of formula —Si(R5)3 where each R5 is independently an alkyl group having 1 to 20 carbon atoms or an aryl group having 5 to 20 carbon atoms.

The term "polymer" refers to both polymeric materials prepared from one monomer such as a homopolymer or to polymeric materials prepared from two or more monomers such as a copolymer, terpolymer, or the like. Likewise, the term "polymerize" refers to the process of making a polymeric material that can be a homopolymer, copolymer, terpolymer, or the like.

The term "mircopores" refers to pores having a diameter less than 2 nanometers.

The term "mesopores" refers to pores having a diameter in a range of 2 to 50 nanometers.

The term "macropores" refer to pores having a diameter greater than 50 nanometers.

In a first aspect, a compound of Formula (I) is provided.

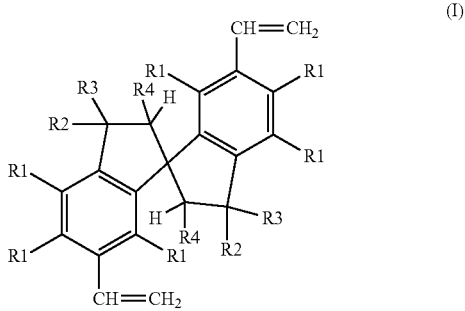

(I)

In Formula (I), each R1 is independently hydrogen, halo, alkyl, aryl, alkaryl, or aralkyl. Each R2 is independently hydrogen, alkyl, alkoxy, aryl, alkaryl, aralkyl, hydroxyl, silyloxy, combines with a R3 connected to a same carbon atom to form a cyclic alkyl, combines with a R3 connected to the same carbon atom to form a cyclic alkyl that is fused to one or more carbocyclic rings, or combines with R3 and the carbon atom to which both R2 and R3 are connected to form a carbonyl group. Each R3 is independently hydrogen, alkyl, alkoxy, aryl, alkaryl, aralkyl, hydroxyl, silyloxy, combines with a R2 connected to a same carbon atom to form a cyclic alkyl, combines with a R2 connected to the same carbon atom to form a cyclic alkyl that is fused to one or more carbocyclic rings, combines with R2 and the carbon to which both R2 and R3 are connected to form a carbonyl group, or combines with R4 connected to adjacent carbon atom to form a carbon-carbon bond. Each R4 is independently hydrogen or combines with R3 connected to an adjacent carbon atom to form a carbon-carbon bond.

Each R1 is independently hydrogen, halo, alkyl, aryl, alkaryl, or aralkyl. Suitable halo groups include, but are not limited to, chloro and bromo. Suitable alkyl groups often have up to 20 carbon atoms, up to 10 carbon atoms, up to 6 carbon atoms, or up to 4 carbon atoms. For example, the alkyl groups can have 1 to 10 carbon atoms, 3 to 10 carbon atoms, 1 to 6 carbon atoms, 3 to 6 carbon atoms, or 1 to 4 carbon atoms. Suitable aryl groups often have up to 12 carbon atoms, up to 10 carbon atoms, or up to 6 carbon atoms. In many embodiments, the aryl group is phenyl. Suitable alkaryl and aralkyl groups often have an aryl group with up to 12 carbon atoms, up to 10 carbon atoms, or up to 6 carbon atoms and an alkyl group with up to 10 carbon atoms, up to 6 carbon atoms, or up to 4 carbon atoms. An example alkaryl group is phenyl substituted with one or more alkyl groups having 1 to 10 carbon atoms, 1 to 6 carbon atoms, or 1 to 4 carbon atoms. An example aralkyl group is an alkyl group having 1 to 10 carbon atoms, 1 to 6 carbon atoms, or 1 to 4 carbon atoms substituted with a phenyl.

Each R2 is independently hydrogen, alkyl, alkoxy, aryl, alkaryl, aralkyl, hydroxyl, silyloxy, combines with a R3 connected to a same carbon atom to form a cyclic alkyl, combines with a R3 connected to the same carbon atom to form a cyclic alkyl that is fused to one or more carbocyclic rings, or combines with R3 and the carbon atom to which both R2 and R3 are connected to form a carbonyl group. Suitable alkyl and alkoxy groups often have up to 20 carbon atoms, up to 10 carbon atoms, up to 6 carbon atoms, or up to 4 carbon atoms. For example, the alkyl and alkoxy groups can have 1 to 10 carbon atoms, 3 to 10 carbon atoms, 1 to 6 carbon atoms, 3 to 6 carbon atoms, or 1 to 4 carbon atoms. Suitable aryl groups often have up to 12 carbon atoms, up to 10 carbon atoms, or up to 6 carbon atoms. In many embodiments, the aryl group is phenyl. Suitable alkaryl and aralkyl groups often have an aryl group with up to 12 carbon atoms, up to 10 carbon atoms, or up to 6 carbon atoms and an alkyl group with up to 10 carbon atoms, up to 6 carbon atoms, or up to 4 carbon atoms. An example alkaryl group is phenyl substituted with one or more alkyl groups having 1 to 10 carbon atoms, 1 to 6 carbon atoms, or 1 to 4 carbon atoms. An example aralkyl group is an alkyl group having 1 to 10 carbon atoms, 1 to 6 carbon atoms, or 1 to 4 carbon atoms substituted with a phenyl. Suitable silyloxy groups are of formula —Si(R5)3 where each R5 is independently an alkyl group having 1 to 20 carbon atoms or an aryl group having 5 to 20 carbon atoms. Example R5 groups include, but are not limited to, phenyl and alkyl groups having 1 to 10 carbon atoms, 1 to 6 carbon atoms, or 1 to 3 carbon atoms. Suitable cyclic alkyl groups that form through the combination of R2 and R3 can have up to 10 carbon atoms, up to 8 carbon atoms, or up to 6 carbon atoms. In many embodiments, the cyclic alkyl group has 3 to 8 carbon atoms or 3 to 6 carbon atoms. The cyclic alkyl group can optionally be fused to one or more carbocyclic rings. Each carbocyclic ring typically has up to 10 carbon atoms, up to 8 carbon atoms, or up to 6 carbon atoms and can be aromatic (i.e., unsaturated), partially unsaturated, or saturated. The fused carbocyclic rings are often benzene rings. An example cyclic alkyl with one or more fused carbocyclic rings is fluorenyl (i.e., a monovalent radical of flourene).

Each R3 is independently hydrogen, alkyl, alkoxy, aryl, alkaryl, aralkyl, hydroxyl, silyloxy, combines with a R2 connected to a same carbon atom to form a cyclic alkyl, combines with a R2 connected to the same carbon atom to form a cyclic alkyl that is fused to one or more carbocyclic rings, combines with R2 and the carbon to which both R2 and R3 are connected to form a carbonyl group, or combines with R4 connected to adjacent carbon atom to form a carbon-carbon bond.

Suitable alkyl and alkoxy groups often have up to 20 carbon atoms, up to 10 carbon atoms, up to 6 carbon atoms, or up to 4 carbon atoms. For example, the alkyl and alkoxy groups can have 1 to 10 carbon atoms, 3 to 10 carbon atoms, 1 to 6 carbon atoms, 3 to 6 carbon atoms, or 1 to 4 carbon atoms. Suitable aryl groups often have up to 12 carbon atoms, up to 10 carbon atoms, or up to 6 carbon atoms. In many embodiments, the aryl group is phenyl. Suitable alkaryl and aralkyl groups often have an aryl group with up to 12 carbon atoms, up to 10 carbon atoms, or up to 6 carbon atoms and an alkyl group with up to 10 carbon atoms, up to 6 carbon atoms, or up to 4 carbon atoms. An example alkaryl group is phenyl substituted with one or more alkyl groups having 1 to 10 carbon atoms, 1 to 6 carbon atoms, or 1 to 4 carbon atoms. An example aralkyl group is an alkyl group having 1 to 10 carbon atoms, 1 to 6 carbon atoms, or 1 to 4 carbon atoms substituted with a phenyl. Suitable silyloxy groups are of formula —Si(R5)3 where each R5 is independently an alkyl group having 1 to 20 carbon atoms or an aryl group having 5 to 20 carbon atoms. Example R5 groups include, but are not limited to, phenyl and alkyl groups having 1 to 10 carbon atoms, 1 to 6 carbon atoms, or 1 to 3 carbon atoms. Suitable cyclic alkyl groups that form through the combination of R2 and R3 can have up to 10 carbon atoms, up to 8 carbon atoms, or up to 6 carbon atoms. In many embodiments, the cyclic alkyl group has 3 to 8 carbon atoms or 3 to 6 carbon atoms. The cyclic alkyl group can optionally be fused to one or more carbocyclic rings. Each carbocyclic ring typically has up to 10 carbon atoms, up to 8 carbon atoms, or up to 6 carbon atoms and can be aromatic (i.e., unsaturated), partially unsaturated, or saturated. The fused carbocyclic rings are often benzene rings. An example cyclic alkyl with one or more fused carbocyclic rings is fluorenyl (i.e., a monovalent radical of flourene).

Each R4 is independently hydrogen or combines with R3 connected to an adjacent carbon atom to form a carbon-carbon bond.

In some more specific embodiments of the monomer of Formula (I), R1 is hydrogen or halo, R2 is alkyl having 1 to 10 carbon atoms (e.g., 1 to 6 carbon atoms, 1 to 4 carbon atoms, 1 to 3 carbon atoms, or 1 carbon atom), R3 is alkyl having 1 to 10 carbon atoms (e.g., 1 to 6 carbon atoms, 1 to 4 carbon atoms, 1 to 3 carbon atoms, or 1 carbon atom), and R4 is hydrogen. In an even more specific embodiment of the monomer of Formula (I), R1 is hydrogen, R2 is methyl, R3 is methyl, and R4 is hydrogen; this monomer is 3,3,3',3'-tetramethyl-1,1'-spirobisindan-6,6'-divinyl.

The monomers of Formula (I) can be prepared using any known method. For example, monomers where R1 and R4 are hydrogen and where R2 and R3 are alkyl can be prepared as shown in Reaction Scheme B.

Reaction Scheme B

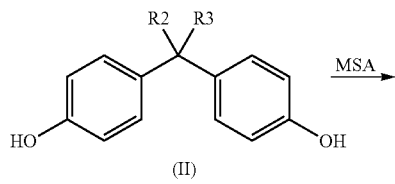

(II)

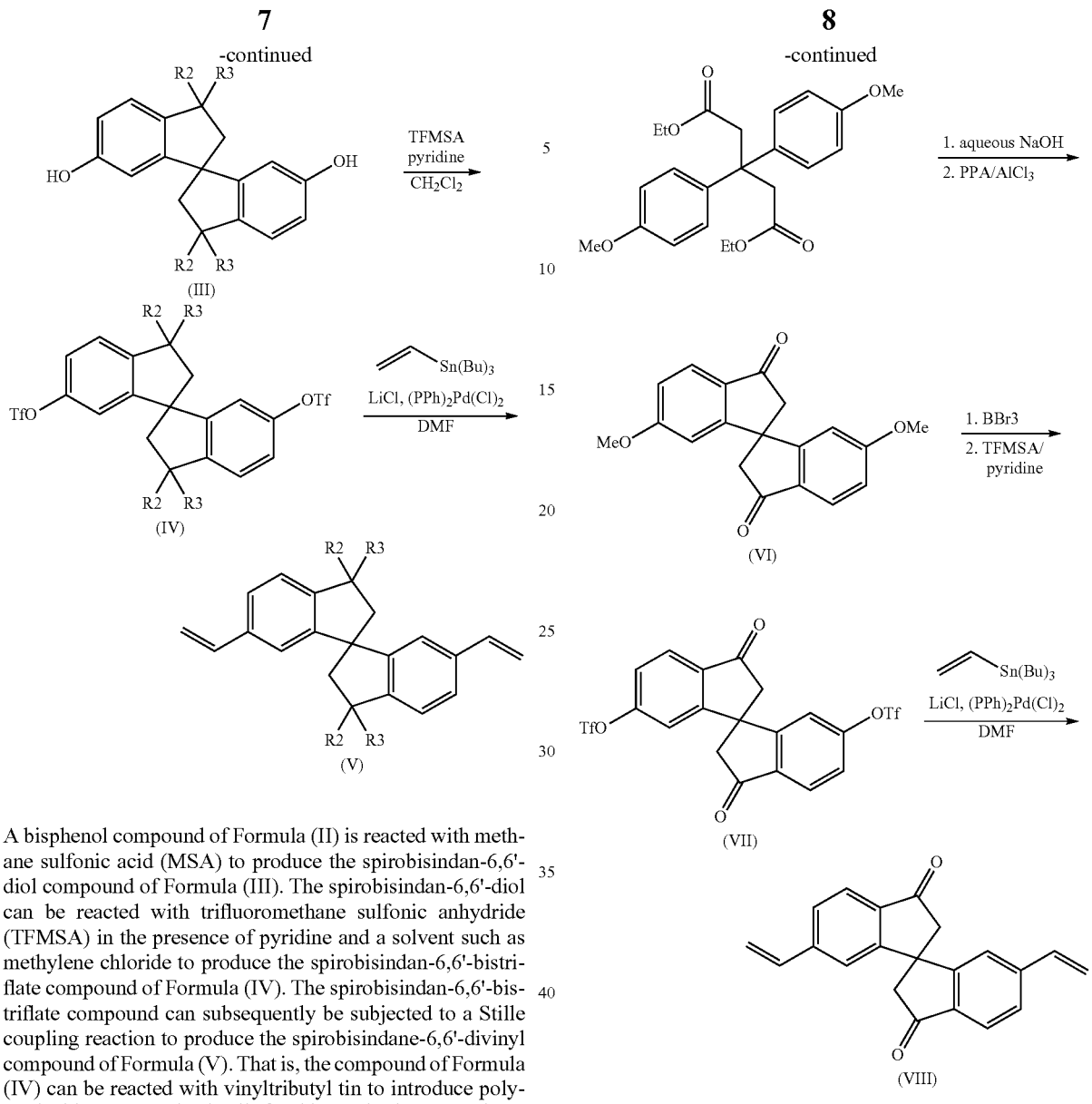

A bisphenol compound of Formula (II) is reacted with methane sulfonic acid (MSA) to produce the spirobisindan-6,6'-diol compound of Formula (III). The spirobisindan-6,6'-diol can be reacted with trifluoromethane sulfonic anhydride (TFMSA) in the presence of pyridine and a solvent such as methylene chloride to produce the spirobisindan-6,6'-bistriflate compound of Formula (IV). The spirobisindan-6,6'-bistriflate compound can subsequently be subjected to a Stille coupling reaction to produce the spirobisindane-6,6'-divinyl compound of Formula (V). That is, the compound of Formula (IV) can be reacted with vinyltributyl tin to introduce polymerizable groups. The details for this synthesis approach are further described in the Example section for the preparation of the monomer 3,3,3',3'-tetramethyl-1,1'-spirobisindan-6,6'-divinyl starting from bisphenol A as the compound of Formula (II).

Compounds of Formula (I) where R2 and R3 combine with the carbon atom to which both R2 and R3 are connected to form a carbonyl group can be prepared as shown in Reaction Scheme C.

Reaction Scheme C

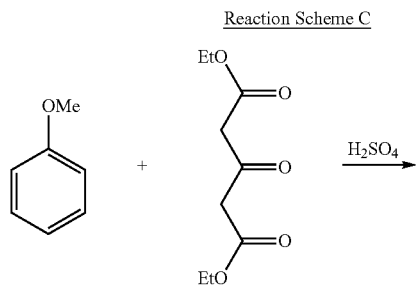

The chemistry involved in the formation of the dione (Compound (VI)) is described in Org. Lett., 10, 2641-2643 (2008). More specifically, diethyl-1,3-acetonedicarboxylate and methoxybenzene are reacted in the presence of sulfuric acid. This reaction is followed by hydrolysis and then Friedel-Crafts acylation mediated by polyphosphoric acid (PPA). The dione (Compound (VI)) is then reacted with $BBr_3$ to convert the methoxy groups to hydroxyl groups. The hydroxyl groups are then reacted with trifluoromethane sulfonic anhydride in the presence of pyridine and a solvent such as methylene chloride to produce the triflate groups in Compound (VII). The triflate groups can be reacted with vinyltributyl tin to introduce the polymerizable groups in Compound (VIII).

The dione (Compound (VI)) can be used as a precursor to prepare various other monomers of Formula (I) using Grignard reactions. By the appropriate selection of the Grignard reagent, this method can be used in the preparation of a compound of Formula (I) where R2 or R3 is an alkyl, aryl, alkaryl, or aralkyl. This type of reaction is exemplified using phenyl magnesium bromide as the Grignard reagent in Reaction Scheme D.

Reaction Scheme D

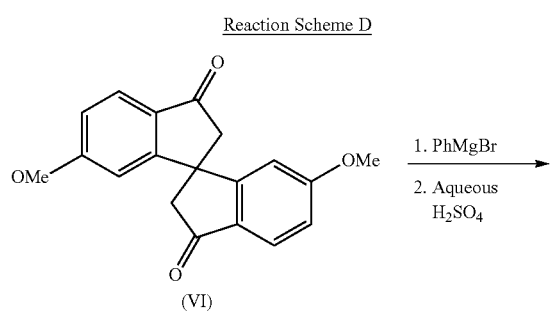

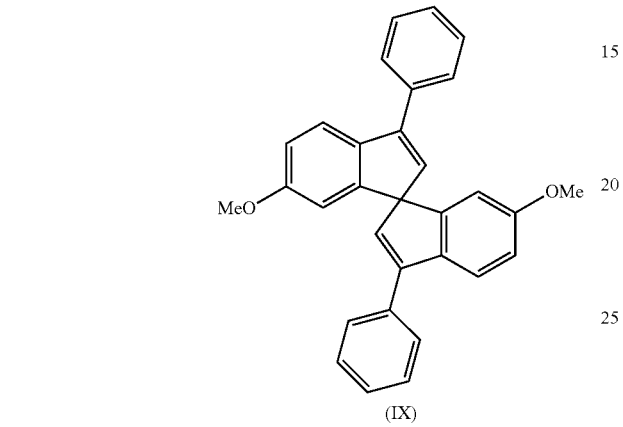

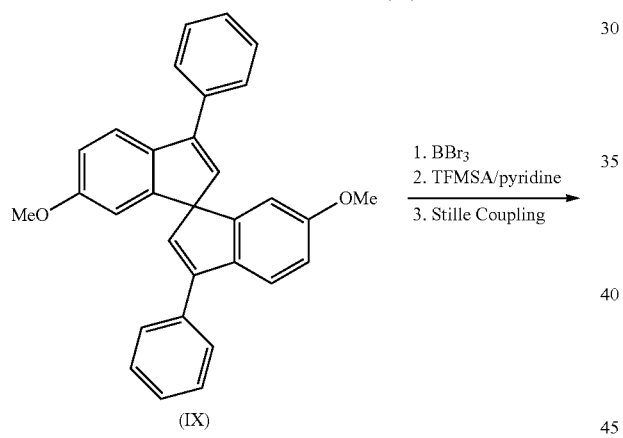

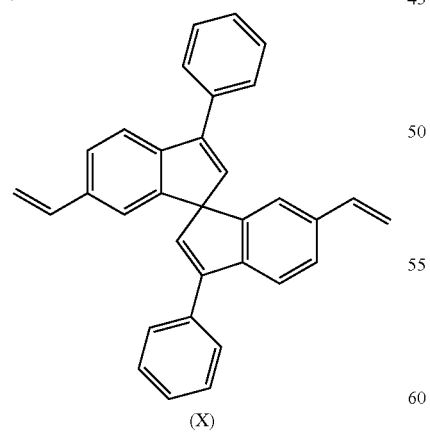

The dehydrated bisindane (Compound (IX)) is formed after treatment with aqueous sulfuric acid. The methoxy groups in Compound (IX) can be converted to vinyl groups as in Reaction Scheme C resulting in the formation of Compound (X).

A more complex Grignard reagent such as biphenyl magnesium bromide can be used as well. This reaction is shown in Reaction Scheme E where spirofluorene groups are introduced to prepare Compound (XI). This can be converted to the divinyl Compound (XII) using the same three reactions described for Reaction Schemes C and D.

Reaction Scheme E

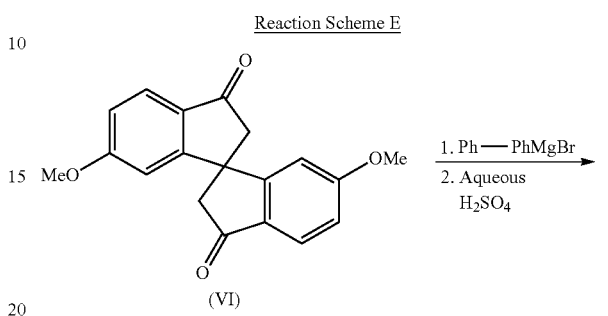

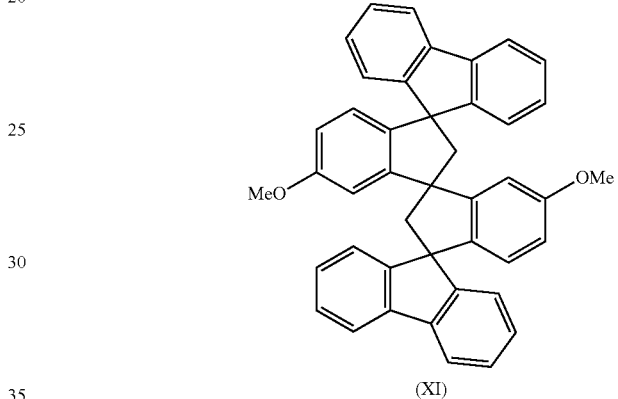

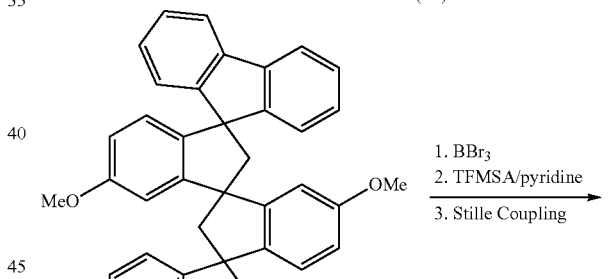

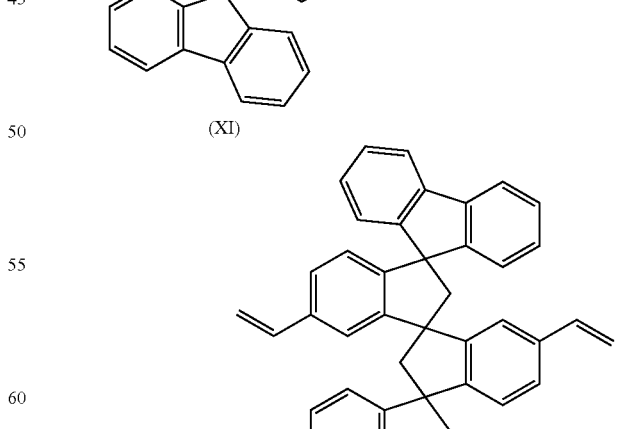

Compound (VII) can be used to prepare a compound of Formula (I) where R2 or R3 is an hydroxyl group. This is illustrated in Reaction Scheme F. A strong base can be reacted with Compound (VII) to form Compound (XIII). The triflate groups in Compound (XIII) can be changed to vinyl groups using a Stille coupling reaction as described in Reaction Scheme A to prepare Compound (XIV).

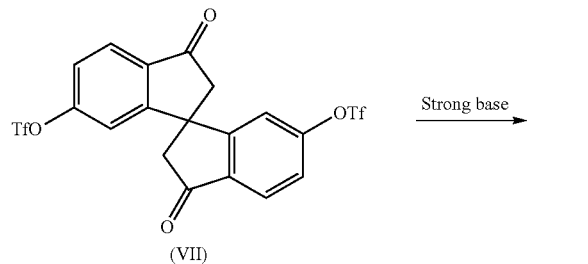

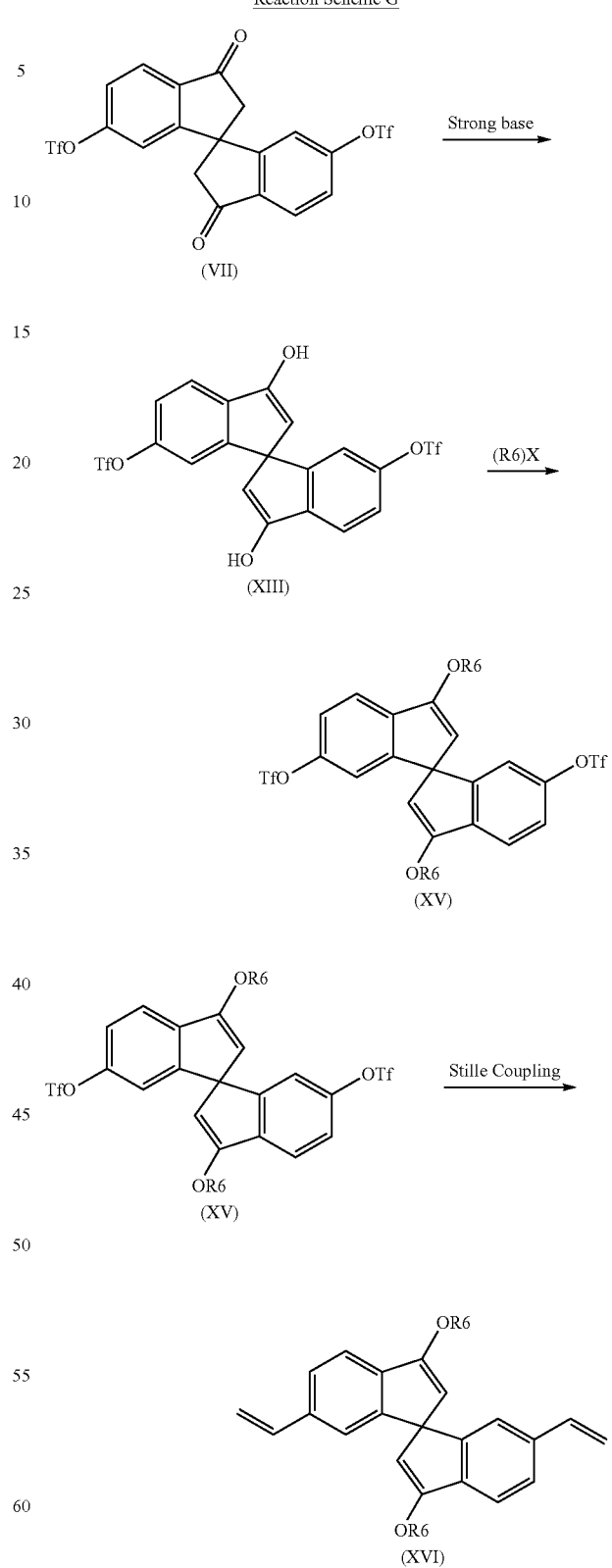

Where R2 or R3 in the monomer of Formula (I) is alkoxy or silyloxy, a strong base can be used to convert Compound (VII) to Compound (XIII) as in Reaction Scheme F. Then, as shown in Reaction Scheme G, Compound (XIII) can be reacted with a compound (R6)X where X is halo and R6 is an alkyl or silyl of formula —Si(R5)$_3$ and where R5 is alkyl or aryl. The product is Compound (XV) with two —OR6 groups. This compound can be converted to the divinyl Compound (XVI) using a Stille coupling reaction as described for Reaction Scheme A.

In another aspect, an intermediate of Formula (XVI) is provided that is used in the preparation of the compound of Formula (I).

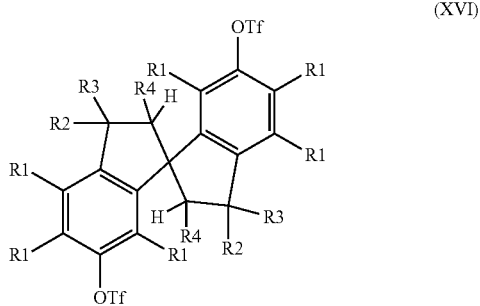

(XVI)

In Formula (XVI), the group —OTf is triflate (—OSO$_2$CF$_3$). The groups R1, R2, R3, and R4 are the same as described above for the compound of Formula (I). In some more specific embodiments of the monomer of Formula (XVI), R1 is hydrogen or halo, R2 is alkyl having 1 to 10 carbon atoms (e.g., 1 to 6 carbon atoms, 1 to 4 carbon atoms, 1 to 3 carbon atoms, or 1 carbon atom), R3 is alkyl having 1 to 10 carbon atoms (e.g., 1 to 6 carbon atoms, 1 to 4 carbon atoms, 1 to 3 carbon atoms, or 1 carbon atom), and R4 is hydrogen. In an even more specific embodiment of the monomer of Formula (XVI), R1 is hydrogen, R2 is methyl, R3 is methyl, and R4 is hydrogen. One example compound of Formula (XVI) is 3,3,3',3'-tetramethyl-1,1'-spirobisindan-6,6'-bistriflate, which can also be referred to as perfluoromethane-1-sulfonic acid 6'-(perfluoromethane-1-sulfonyloxy)-3,3,3',3'-tetramethyl-1,1'-spirobisindane-6-yl ester.

In another aspect, a polymerizable composition is provided. The polymerizable composition comprises a monomer of Formula (I) as described above. In some embodiments, a single type of monomer of Formula (I) is included in the polymerizable composition and the polymerized product formed is a homopolymer. In other embodiments, the polymerizable composition includes more than one type of monomer. Such polymerizable compositions can contain multiple types of monomers of Formula (I) or can contain at least one type of monomer of Formula (I) and at least one co-monomer that is not of Formula (I).

The co-monomers are often selected to prepare a polymerized product that is a porous polymeric material. In some embodiments, the co-monomers include one or more polyvinyl aromatic monomers. The term "polyvinyl aromatic monomer" refers to a monomer that is not of Formula (I) and that has a plurality (e.g., two or three) of vinyl groups that are each bonded to an aromatic carbocyclic group. The aromatic carbocyclic group has at least one aromatic carbocyclic ring and can have 1 to 5 optional rings that are connected to or fused to the aromatic carbocyclic ring. The additional rings can be aromatic, aliphatic, or a combination thereof. Any of the rings optionally can be substituted with one or more alkyl groups. The aromatic carbocyclic group usually has 5 to 20 carbon atoms or 6 to 20 carbon atoms. The polyvinyl aromatic monomer is often a divinyl aromatic monomer (e.g., divinylbenzene or divinylbenzene substituted with one or more alkyl groups) or a trivinyl aromatic monomer (e.g., trivinylbenzene or trivinylbenzene substituted with one or more alkyl groups).

Such polymerizable compositions often contain at least 1 weight percent, at least 5 weight percent, at least 10 weight percent, at least 20 weight percent, at least 30 weight percent, at least 40 weight percent, or at least 50 weight percent of a monomer of Formula (I). For the preparation of polymeric material with micropores, the polymerizable composition often contains at least 50 weight percent, at least 60 weight percent, at least 70 weight percent, at least 80 weight percent, or at least 90 weight percent of the monomer of Formula (I). In some embodiments, the polymerizable composition can include 1 to 99 weight percent of a monomer of Formula (I) and 1 to 99 weight percent of a polyvinyl aromatic monomer. For example, the polymerizable composition can contain 10 to 90 weight percent of a monomer of Formula (I) and 10 to 90 weight percent of a polyvinyl aromatic monomer, 20 to 80 weight percent of a monomer of Formula (I) and 20 to 80 weight percent of a polyvinyl aromatic monomer, 30 to 70 weight percent of a monomer of Formula (I) and 30 to 70 weight percent of a polyvinyl aromatic monomer, or 40 to 60 weight percent of a monomer of Formula (I) and 40 to 60 weight percent of a polyvinyl aromatic monomer. The weight percent is based on a total weight of monomer in the polymerizable composition.

Some polyvinyl aromatic monomers contain one or more mono-vinyl aromatic monomers as impurities. As used herein, the term "mono-vinyl aromatic monomer" refers to a monomer having a single vinyl group bonded to an aromatic carbocyclic group. The aromatic carbocyclic group has at least one aromatic carbocyclic ring and can have 1 to 5 optional rings that are connected to or fused to the aromatic carbocyclic ring. The additional rings can be aromatic, aliphatic, or a combination thereof. Any of the rings optionally can be substituted with one or more alkyl groups. The aromatic carbocyclic group usually has 5 to 20 carbon atoms or 6 to 20 carbon atoms. Example mono-vinyl aromatic monomers include, but are not limited to, styrene, ethyl styrene, and the like.

In some embodiments, the polyvinyl aromatic monomer contains up to 25 weight percent, up 20 weight percent, up to 15 weight percent, up to 10 weight percent, or up to 5 weight percent mono-vinyl aromatic monomer. For example, technical grade divinylbenzene typically contains about 20 weight percent ethyl styrene. The weight percent is based on a total weight of the mono-vinyl aromatic monomer and the polyvinyl aromatic monomer.

Considering impurities that may be present in the polyvinyl aromatic monomers, the polymerizable compositions often contain 1 to 99 weight percent of a monomer of Formula (I), 0 to 25 weight percent of mono-vinyl aromatic monomer, and 1 to 99 weight percent of a polyvinyl aromatic monomer. In another example, the polymerizable composition contains 1 to 98 weight percent of a monomer of Formula (I), 1 to 20 weight percent of a mono-vinyl aromatic monomer, and 1 to 98 weight percent of a polyvinyl aromatic monomer. In yet another example, the polymerizable composition contains 5 to 90 weight percent of a monomer of Formula (I), 5 to 19 weight percent of a mono-vinyl aromatic monomer, and 5 to 90 weight percent of a polyvinyl aromatic monomer of Formula (I). If polymeric material that is porous is desired, the amount of mono-vinyl aromatic monomer is typically selected to be less than 15 weight percent, less than 10 weight percent, or less than 5 weight percent. The weight percent is based on a total weight of monomer in the polymerizable composition.

In addition to the various monomers, the polymerizable compositions typically include an initiator for free radical polymerization reactions. Any suitable free radical initiator can be used. In some embodiments, the free radical initiator is a thermal initiator that is usually activated at a temperature above room temperature. In other embodiments, the free radical initiator is a redox initiator. Suitable free radical initiators are typically selected to be miscible with the monomers included in the polymerizable composition. The free radical initiator is typically present in an amount in a range of 0.05 to 10 weight percent, in a range of 0.05 to 5 weight percent, in a range of 0.05 to 2 weight percent, in a range of 0.05 to 1 weight percent, in a range of 0.1 to 5 weight percent, in a range of 0.2 to 5 weight percent, in a range of 0.5 to 5 weight percent, in a range of 0.1 to 2 weight percent, or in a range of 0.1 to 1 weight percent. The weight percent is based on a total weight of monomer in the polymerizable composition. Both the type and amount of initiator can affect the polymerization rate, which in turn can influence the formation of porous polymeric material.

Suitable thermal initiators include, but are not limited to, organic peroxides and azo compounds. Example azo compounds include, but are not limited to, those commercially available under the trade designation VAZO from E.I. du Pont de Nemours Co. such as VAZO 64 (2,2'-azobis(isobutyronitrile), which is often referred to as AIBN) and VAZO 52 (2,2'-azobis(2,4-dimethylpentanenitrile)). Other azo compounds are commercially available from Wako Chemicals USA, Inc. (Richmond, Va.) such as V-601 (dimethyl 2,2'-azobis(2-methylproprionate)), V-65 (2,2'-azobis(2,4-dimethyl valeronitrile)), and V-59 (2,2'-azobis(2-methylbutyronitrile)). Organic peroxides include, but are not limited to, bis(1-oxoaryl)peroxides such as benzoyl peroxide (BPO), bis(1-oxoalkyl)peroxides such as lauroyl peroxide, and dialkyl peroxides such as dicumyl peroxide or di-tert-butyl peroxide, and mixtures thereof. The temperature needed to activate the imitator is often in a range of 25° C. to 160° C., 30° C. to 160° C., or 40° C. to 160° C.

Suitable redox initiators include arylsulfinate salts or triarylsulfonium salts in combination with a metal in an oxidized state, a peroxide, or a persulfate. Specific arylsulfinate salts include tetraalkylammonium arylsulfinates such as tetrabutylammonium 4-ethoxycarbonylbenzenesulfinate, tetrabutylammonium 4-trifluoromethylbenzenesulfinate, and tetrabutylammonium 3-trifluoromethylbenzenesulfinate. Specific triarylsulfonium salts include those with a triphenylsulfonium cation and with an anion selected from $PF_6^-$, $AsF_6^-$, and $SbF_6^-$. Suitable metal ions include, for example, ions of group III metals, transition metals, and lanthanide metals. Specific metal ions include, but are not limited to, Fe(III), Co(III), Ag(I), Ag(II), Cu(II), Ce(III), Al(III), Mo(VI), and Zn(II). Suitable peroxides include benzoyl peroxide, lauroyl peroxide, and the like. Suitable persulfates include, for example, ammonium persulfate, tetraalkylammonium persulfate (e.g., tetrabutylammonium persulfate), and the like.

The polymerizable composition typically also includes a solvent. Any suitable solvent or mixture of solvents can be selected. The one or more solvents are typically selected to be miscible with the monomers included in the polymerizable composition. Stated differently, the monomers in the polymerizable composition are typically dissolved in one or more solvents. Additionally, the selection of the one or more solvents can alter the porosity of the polymeric material formed from the polymerizable composition. The porosity can often be increased by delaying the onset of phase separation of the growing polymeric chains during the polymerization process. That is, the use of solvents with good solubility for both the monomers and the growing polymeric material tends to enhance porosity. Solubility parameter calculations can be used to select a solvent or solvent mixture that is close to that of the polymeric material. Solvents that tend to enhance porosity include, but are not limited to, ethyl acetate, amyl acetate (i.e., n-pentyl acetate), and methyl ethyl ketone.

The onset of phase separation of the growing polymeric chains also can be delayed by reducing the rate of polymerization. The rate can be reduced by using a lower polymerization temperature and selecting an initiator that is activated at a lower temperature. The amount of the initiator added to the polymerizable composition can also influence the rate of reaction. That is, the reaction rate is typically increased with the addition of higher amounts of the initiator.

Additionally, the percent solids of the polymerizable composition can influence the rate of polymerization. Typically, lower percent solids tend to favor porosity. The percent solids are often in a range of 0.5 to 50 weight percent, 1 to 40 weight percent, 1 to 30 weight percent, 1 to 20 weight percent, 1 to 15 weight percent, 1 to 10 weight percent, 1 to 6 weight percent, or 2 to 6 weight percent based on a total weight of the polymerizable composition.

Other types of polymerization methods can be used, if desired, such as, for example, emulsion polymerization methods and suspension polymerization methods. If porous polymeric material is desired, the polymerizable compositions and reaction conditions can be selected using the principles discussed above.

In another aspect, polymeric material is provided that is a reaction product of the polymerizable composition. The polymerized product can be a monolith that can be easily broken apart for washing to remove any residual monomer. The washed product can be dried to form a powder. Alternatively, if suspension polymerization or emulsion polymerization methods are used, the polymerized product can be in the form of beads or particles.

The polymeric material can be porous. The porosity can be characterized from adsorption isotherms obtained at various relative pressures (e.g., $10^{-6}$ to 0.98) using nitrogen or argon as the sorbate under cryogenic conditions. The total porosity can be calculated based on the total amount of nitrogen adsorbed at a relative pressure close to 0.95 or higher. The total porosity is often at least 0.30 $cm^3$/gram, at least 0.35 $cm^3$/gram, at least 0.40 $cm^3$/gram, or at least 0.45 $cm^3$/gram. The total porosity can be, for example, up to 1.0 $cm^3$/gram or higher, up to 0.95 $cm^3$/gram, or up to 0.90 $cm^3$/gram.

The total porosity and the pore size distribution can be varied by choice of monomers in the polymerizable composition and the reaction conditions such as solvent selection, the percent solids of the polymerizable composition, and the polymerization rate. In many embodiments, the porous polymeric material is microporous, mesoporous, or both. Homopolymers prepared from polymerizable compositions containing a monomer of Formula (I) tend to be microporous. Depending on the specific reaction conditions, the porosity can be predominately microporous. Various polyvinyl aromatic monomers that are not of Formula (I) can be added to the polymerizable composition to prepare polymeric material having both micropores and mesopores. As the amount of the polyvinyl aromatic monomer is increased relative to the monomer of Formula (I), the percentage of the total porosity attributable to micropores tends to decrease.

For some applications, polymeric material having a porosity that is mainly microporous can be advantageous. Micropores are particularly well suited, for example, for sorption of organic vapors at low concentrations (e.g., 500 ppm or less). That is, pores with a diameter less than 2 nanometers are comparable in size to the sorbate molecules. This similarity in size tends to favor sorption of the sorbate molecules into the pores.

The total surface area can be calculated from BET (Brunauer-Emmett, and Teller) analysis of the isotherm data at relative pressures less than 0.35, less than 0.30, less than 0.25, or less than 0.20. The total surface area is often at least 300 $m^2$/gram, at least 400 $m^2$/gram, at least 500 $m^2$/gram, or at least 600 $m^2$/gram. The total surface area can be, for example, up to 1000 m²/gram or higher, up to 900 m²/gram, up to 850 m²/gram, or up to 800 m²/gram.

Unlike polymers prepared according to Reaction Scheme A and as further described in U.S. Pat. No. 7,690,514 (McKeown et al.), the polymeric materials prepared from a monomer of Formula (I) are crosslinked. Thus, the polymeric material prepared using the monomers of Formula (I) tend to swell less when placed into a solvent. This may be desirable for some applications where a dimensional change may be undesirable when contacted with a solvent.

Various items are provided including compounds (i.e., monomers), polymerizable compositions, polymeric material, and intermediates in the preparation of the monomers.

Item 1 is a compound of Formula (I).

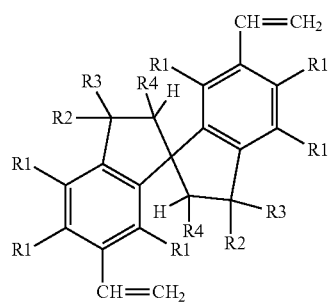

In Formula (I), each R1 is independently hydrogen, halo, alkyl, aryl, alkaryl, or aralkyl. Each R2 is independently hydrogen, alkyl, alkoxy, aryl, alkaryl, aralkyl, hydroxyl, silyloxy, combines with a R3 connected to a same carbon atom to form a cyclic alkyl, combines with a R3 connected to the same carbon atom to form a cyclic alkyl that is fused to one or more carbocyclic rings, or combines with R3 and the carbon atom to which both R2 and R3 are connected to form a carbonyl group. Each R3 is independently hydrogen, alkyl, alkoxy, aryl, alkaryl, aralkyl, hydroxyl, silyloxy, combines with a R2 connected to a same carbon atom to form a cyclic alkyl, combines with a R2 connected to the same carbon atom to form a cyclic alkyl that is fused to one or more carbocyclic rings, combines with R2 and the carbon to which both R2 and R3 are connected to form a carbonyl group, or combines with R4 connected to adjacent carbon atom to form a carbon-carbon bond. Each R4 is independently hydrogen or combines with R3 connected to an adjacent carbon atom to form a carbon-carbon bond.

Item 2 is the compound of item 1, wherein each R1 is hydrogen or halo.

Item 3 is the compound of item 1 or 2, wherein each R2 and each R3 are alkyl.

Item 4 is the compound of any one of items 1 to 3, wherein R4 is hydrogen.

Item 5 is the compound of any one of item 1 to 4, wherein the compound is 3,3,3',3'-tetramethyl-1,1'-spirobisindan-6,6'-divinyl.

Item 6 is a polymerizable composition comprising a compound of Formula (I).

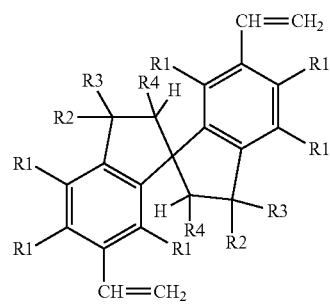

In Formula (I), each R1 is independently hydrogen, halo, alkyl, aryl, alkaryl, or aralkyl. Each R2 is independently hydrogen, alkyl, alkoxy, aryl, alkaryl, aralkyl, hydroxyl, silyloxy, combines with a R3 connected to a same carbon atom to form a cyclic alkyl, combines with a R3 connected to the same carbon atom to form a cyclic alkyl that is fused to one or more carbocyclic rings, or combines with R3 and the carbon atom to which both R2 and R3 are connected to form a carbonyl group. Each R3 is independently hydrogen, alkyl, alkoxy, aryl, alkaryl, aralkyl, hydroxyl, silyloxy, combines with a R2 connected to a same carbon atom to form a cyclic alkyl, combines with a R2 connected to the same carbon atom to form a cyclic alkyl that is fused to one or more carbocyclic rings, combines with R2 and the carbon to which both R2 and R3 are connected to form a carbonyl group, or combines with R4 connected to adjacent carbon atom to form a carbon-carbon bond. Each R4 is independently hydrogen or combines with R3 connected to an adjacent carbon atom to form a carbon-carbon bond.

Item 7 is the polymerizable composition of item 6, wherein the polymerizable composition further comprises a polyvinyl aromatic monomer or a polyvinyl aromatic monomer substituted with one or more alkyl groups.

Item 8 is the polymerizable composition of item 7, wherein the polyvinyl aromatic monomer is divinylbenzene, trivinylbenzene, divinylbenzene substituted with one or more alkyl groups, or trivinylbezene substituted with one or more alkyl groups.

Item 9 is the polymerizable composition of any one of items 6 to 8, further comprising up to 25 weight percent of a mono-vinyl aromatic monomer or a mono-vinyl aromatic monomer substituted with one or more alkyl groups.

Item 10 is the polymerizable composition of item 9, wherein polymerizable composition comprises the 1 to 99 weight percent of a monomer of Formula (I), 0 to 25 weight percent of mono-vinyl aromatic monomer, and 1 to 99 weight percent of a polyvinyl aromatic monomer, wherein the weight percents are based on a total weight of monomers in the polymerizable composition.

Item 11 is the polymerizable composition of any one of items 6 to 10, wherein each R1 is hydrogen or halo.

Item 12 is the polymerizable composition of any one of items 6 to 11, wherein each R2 and each R3 are alkyl.

Item 13 is the polymerizable composition of any one of items 6 to 12, wherein R4 is hydrogen.

Item 14 is the polymerizable composition of any one of items 6 to 13, wherein the compound of Formula (I) is 3,3,3',3'-tetramethyl-1,1'-spirobisindan-6,6'-divinyl.

Item 15 is a polymer comprising the polymerized product of a polymerizable composition comprising a compound of Formula (I).

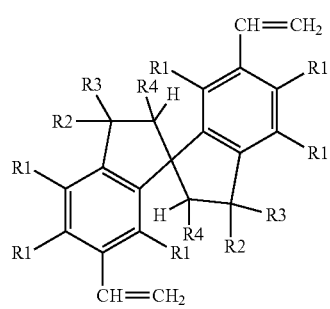

(I)

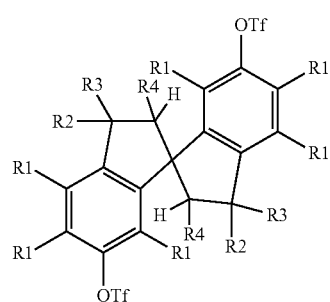

(XVI)

In Formula (I), each R1 is independently hydrogen, halo, alkyl, aryl, alkaryl, or aralkyl. Each R2 is independently hydrogen, alkyl, alkoxy, aryl, alkaryl, aralkyl, hydroxyl, silyloxy, combines with a R3 connected to a same carbon atom to form a cyclic alkyl, combines with a R3 connected to the same carbon atom to form a cyclic alkyl that is fused to one or more carbocyclic rings, or combines with R3 and the carbon atom to which both R2 and R3 are connected to form a carbonyl group. Each R3 is independently hydrogen, alkyl, alkoxy, aryl, alkaryl, aralkyl, hydroxyl, silyloxy, combines with a R2 connected to a same carbon atom to form a cyclic alkyl, combines with a R2 connected to the same carbon atom to form a cyclic alkyl that is fused to one or more carbocyclic rings, combines with R2 and the carbon to which both R2 and R3 are connected to form a carbonyl group, or combines with R4 connected to adjacent carbon atom to form a carbon-carbon bond. Each R4 is independently hydrogen or combines with R3 connected to an adjacent carbon atom to form a carbon-carbon bond.

Item 16 is the polymer of item 15, wherein the polymerizable composition further comprises a polyvinyl aromatic monomer or a polyvinyl aromatic monomer substituted with one or more alkyl group.

Item 17 is the polymer of item 15 or 16, wherein the polymer is porous.

Item 18 is the polymer of item 17, wherein the polymer is microporous, mesoporous, or both.

Item 19 is the polymer of any one of items 15 to 18, wherein polymerizable composition comprises the 1 to 99 weight percent of a monomer of Formula (I), 0 to 25 weight percent of mono-vinyl aromatic monomer, and 1 to 99 weight percent of a polyvinyl aromatic monomer, wherein the weight percents are based on a total weight of monomers in the polymerizable composition.

Item 20 is the polymer of any one of items 15 to 19, wherein the BET surface area is at least 300 m$^2$/gram.

Item 21 is the polymer of any one of items 15 to 20, wherein each R1 is hydrogen or halo.

Item 22 is the polymer of any one of items 15 to 21, wherein each R2 and each R3 are alkyl.

Item 23 is the polymer of any one of items 15 to 22, wherein R4 is hydrogen.

Item 24 is the polymer of any one of items 16 to 23, wherein the compound of Formula (I) is 3,3,3',3'-tetramethyl-1,1'-spirobisindan-6,6'-divinyl.

Item 25 is a compound of Formula (XVI).

In Formula (XVI), each R1 is independently hydrogen, halo, alkyl, aryl, alkaryl, or aralkyl. Each R2 is independently hydrogen, alkyl, alkoxy, aryl, alkaryl, aralkyl, hydroxyl, silyloxy, combines with a R3 connected to a same carbon atom to form a cyclic alkyl, combines with a R3 connected to the same carbon atom to form a cyclic alkyl that is fused to one or more carbocyclic rings, or combines with R3 and the carbon atom to which both R2 and R3 are connected to form a carbonyl group. Each R3 is independently hydrogen, alkyl, alkoxy, aryl, alkaryl, aralkyl, hydroxyl, silyloxy, combines with a R2 connected to a same carbon atom to form a cyclic alkyl, combines with a R2 connected to the same carbon atom to form a cyclic alkyl that is fused to one or more carbocyclic rings, combines with R2 and the carbon to which both R2 and R3 are connected to form a carbonyl group, or combines with R4 connected to adjacent carbon atom to form a carbon-carbon bond. Each R4 is independently hydrogen or combines with R3 connected to an adjacent carbon atom to form a carbon-carbon bond. Each group —OTf is triflate.

Item 26 is the compound of item 25, wherein each R1 is hydrogen or halo.

Item 27 is the compound of item 25 or 26, wherein each R2 and each R3 are alkyl.

Item 28 is the compound of any one of items 25 to 27, wherein R4 is hydrogen.

Item 29 is the compound of any one of items 25 to 28, wherein the compound of Formula (XVI) is perfluoromethane-1-sulfonic acid 6'-(perfluoromethane-1-sulfonyloxy)-3,3,3',3'-tetramethyl-1,1'-spirobisindane-6-yl ester.

EXAMPLES

TABLE 1

| Glossary of Materials | |
|---|---|
| Chemical Name | Chemical Supplier |
| 4,4'-Isopropylidene diphenol (BPA) | Alfa Aesar, Ward Hill. MA |
| Methane sulfonic acid (MSA) | Alfa Aesar, Ward Hill. MA |
| Methylene chloride (CH$_2$Cl$_2$) | EMD Millipore Chemicals, Billerica, MA |
| Methanol (MeOH) | BDH Merck Ltd., Poole Dorset, UK |
| Pyridine | EM Science, Gibbstown, NJ |
| Trifluoromethane sulfonic acid (TFMSA) | Oakwood Products, West Columbia, SC |
| Concentrated hydrogen chloride (HCl) | EMD Millipore Chemicals, Billerica, MA |
| Sodium bicarbonate (NaHCO$_3$) | J. T. Baker, Phillipsburg, NJ |
| Sodium sulfate (Na$_2$SO$_4$) | BDH Merck Ltd., Poole Dorset, UK |
| N,N-dimethyl formamide (DMF) | Sigma-Aldrich, Milwaukee, WI |
| Vinyltributyl tin | Sigma-Aldrich, Milwaukee, WI |
| Lithium chloride (LiCl) | Mallinckrodt, St. Louis, MO |

TABLE 1-continued

Glossary of Materials

| Chemical Name | Chemical Supplier |
| --- | --- |
| Bis(triphenylphosphine)palladium (II) chloride | Sigma-Aldrich, Milwaukee, WI |
| Diethyl ether (Et$_2$O) | EMD Millipore Chemicals, Billerica, MA |
| Potassium fluoride (KF) | J. T. Baker, Phillipsburg, NJ |
| Ethyl acetate (EtOAc) | EMD Millipore Chemicals, Billerica, MA |
| Petroleum ether (PE) | EMD Millipore Chemicals, Billerica, MA |
| Benzoyl peroxide (BPO) | Sigma-Aldrich, Milwaukee, WI |
| Azoisobutyronitrile (AIBN) | Sigma-Aldrich, Milwaukee, WI |
| Dimethyl 2,2'-azobis(2-methylpropionate) (V-601) | Wako Pure Chemical Industries, Ltd., Osaka, Japan |
| Methyl ethyl ketone (MEK) | J. T. Baker, Phillipsburg, NJ |
| Divinylbenzene (DVB) (80 percent, technical grade); the technical grade contains about 20 weight percent ethyl styrene. The calculation of moles of DVB used to prepare the polymeric material does not take into account the purity. | Sigma-Aldrich, Milwaukee, WI |
| Acetone-D6 (d$_6$-acetone) | Cambridge Isotope Laboratories, Inc., Andover, MA |
| Chloroform-D (CDCl$_3$) | Cambridge Isotope Laboratories, Inc., Andover, MA |

Nitrogen Sorption Analysis

Porosity and gas sorption experiments were performed using an accelerated surface area and porosimetry instrument (ASAP 2020) from Micromeritics Instrument Corporation (Norcross, Ga.). Ultra-high purity nitrogen was used as the sorbate. The following is a typical method used for the characterization of the porosity within the exemplified materials. In a half inch diameter sample tube obtained from Micromeritics, 60-150 milligrams of material was heated at 150° C. under ultra-high vacuum (2-3 micrometers mercury) for 2 hours on the analysis port of the ASAP 2020 to remove residual solvent and other sorbates.

A nitrogen sorption isotherm at 77° K was obtained for the material using low pressure dosing (5 cm$^3$/g) at p/p° less than 0.1 and a pressure table of linearly spaced pressure points from a relative pressure)(p/p° of 0.1 to 0.95. The method made use of the following equilibrium intervals: 90 seconds at relative pressures less than $10^{-5}$, 40 seconds at relative pressures in a range of $10^{-5}$ to 0.1, and 20 seconds at relative pressures greater than 0.1. Helium was used for the free space determination, after nitrogen sorption analysis, both at ambient temperature and at 77° K.

Apparent surface areas were calculated from nitrogen sorption data by multipoint BET analysis. Apparent micropore and mesopore distributions in the range of 4.5-90 Å were calculated from nitrogen sorption data by DFT analysis using the standard nitrogen DFT model. Total pore volume was calculated from the total amount of nitrogen adsorbed at p/p° equal to 0.95. BET, DFT and total pore volume analyses were performed using Micromeritics MicroActive Version 1.01 software.

Preparatory Example 1

Synthesis of 3,3,3',3'-tetramethyl-1,1'-spirobisindan-6,6'-diol (SBI-diol)

In a 5.0 L round bottomed flask, 1000.69 grams (4.38 moles) of 4,4'-isopropylidene diphenol (BPA) was melted. Once all of the BPA was melted, 50.51 grams (0.526 moles) of methane sulfonic acid (MSA) was slowly added. The reaction mixture was stirred for 3 hours under a nitrogen atmosphere maintaining the temperature of the reaction mixture between 135° C. and 150° C. After 3 hours, while still hot, the molten reaction mixture was poured into 2.0 L of deionized water. A brown precipitate formed.

The resulting precipitate was isolated by vacuum filtration and washed with 1.5 L of deionized water. The isolated solid was then put back in the 5.0 L round bottomed flask and 1.5 L of methylene chloride (CH$_2$Cl$_2$) was added. The solid was stirred in the CH$_2$Cl$_2$ at reflux for one hour. The flask was then allowed to cool to room temperature (20° C. to 25° C.), and the flask was placed in a refrigerator (about 0° C.) overnight. The solid was then isolated by vacuum filtration and washed with a minimal amount (about 500 mL) of chilled CH$_2$Cl$_2$. The solid was then placed in a 4.0 L Erlenmeyer flask and dissolved in 900 mL of methanol (MeOH). To this solution was added 190 mL of CH$_2$Cl$_2$. The solution remained clear. The solution was stirred and 1.1 L of deionized water was added in portions. A white precipitate formed, and the mixture was placed in a refrigerator (about 0° C.) overnight. The solid was isolated by vacuum filtration and washed with a minimal amount (about 300 mL) of chilled CH$_2$Cl$_2$. The MeOH/CH$_2$Cl$_2$/H$_2$O precipitation was repeated once more. The solid from the second precipitation was dried in a vacuum oven at 85° C. overnight to yield 214.77 grams (48 percent) of SBI-diol. $^1$H NMR (500 MHz, acetone-d$_6$) δ 7.85 (s, 2H), 7.02 (d, J=8.1 Hz, 2H), 6.68 (dd, J=8.1, 2.4 Hz, 2H), 6.19 (d, J=2.4 Hz, 2H), 2.32 (d, J=13.0 Hz, 2H), 2.19 (d, J=13.0 Hz, 2H), 1.35 (s, 6H), 1.29 (s, 6H).

Preparatory Example 2

Synthesis of perfluoromethane-1-sulfonic acid 6'-(perfluoromethane-1-sulfonyloxy)-3,3,3',3'-tetramethyl-1,1'-spirobisindane-6-yl ester (SBI-bistriflate)

In a 250 mL round bottomed flask, 5.0025 g (16.2 mmoles) of SBI-diol and 4.755 mL (47.1 mmoles) of pyridine were dissolved in 150 mL of CH$_2$Cl$_2$. The flask was placed in an ice/water bath. To this solution was added dropwise 7.930 mL (58.8 mmoles) of trifluoromethane sulfonic anhydride (TFMSA). After the addition was complete, the flask was removed from the ice/water bath. The reaction mixture was stirred at room temperature under a nitrogen atmosphere for 1 hour. The reaction was stopped by adding 10 mL of aqueous hydrochloric acid (HCl) (10 percent by weight).

The resulting mixture was partitioned between CH$_2$Cl$_2$ and a saturated aqueous solution of sodium bicarbonate (NaHCO$_3$). The organic layer was isolated, dried over anhydrous sodium sulfate (Na$_2$SO$_4$) and filtered. The filtrate was condensed under reduced pressure and dried under high vacuum at room temperature for 3 hours to remove any residual pyridine. The resulting tan solid (SBI-bistriflate) weighed 8.51 grams (92 percent). $^1$H NMR (500 MHz, CDCl$_3$) δ 7.17 (d, J=8.3 Hz, 2H), 7.08 (dd, J=8.3, 2.3 Hz, 2H), 6.55 (d, J=2.3 Hz, 2H), 2.26 (ABq, J=13.2 Hz, 4H), 1.34 (s, 6H), 1.29 (s, 6H). $^{19}$F NMR (470.5 MHz, CDCl$_3$) δ −73.0.

Preparatory Example 3

Synthesis of 3,3,3',3'-tetramethyl-1,1'-spirobisindan-6,6'-divinyl (SBI-divinyl)

In a 250 mL round bottomed flask, 5.0025 grams (8.74 mmoles) of SBI-bistriflate was dissolved in 75 mL of anhydrous N,N-dimethyl formamide (DMF). To this solution was added 6.125 mL (21.0 mmoles) of vinyltributyl tin and 22.2225 grams (52.4 mmoles) of lithium chloride (LiCl). The reaction mixture was stirred at room temperature under a nitrogen atmosphere for 5 minutes before adding 0.6140 g (875 micromoles) of bis(triphenylphosphine)palladium (II) chloride. The reaction mixture was stirred at room temperature overnight under a nitrogen atmosphere. After reacting for 24 hours at room temperature, the reaction was stopped by pouring the reaction mixture into 150 mL of deionized water. A precipitate formed.

The aqueous layer and precipitate were extracted with diethyl ether ($Et_2O$) (3×200 mL). The organic layers were combined. The organic layer was then stirred vigorously at room temperature with an equal volume of aqueous potassium fluoride (KF) (10 grams/100 mL) for 1 hour. A gray-white precipitate formed and the mixture was vacuum filtered. The filtrate was then placed back in a separatory funnel and the organic layer isolated. The organic layer was then dried over anhydrous $Na_2SO_4$ and filtered. The filtrate was condensed under reduced pressure to yield a white solid. This solid was further purified by silica gel chromatography. The material was loaded onto a silica gel column (8×25 cm), and the column was eluted with 5% ethyl acetate (EtOAc)/95% petroleum ether (PE) (vol./vol.). Fractions containing the pure SBI-divinyl were combined, condensed under reduced pressure and dried under high vacuum at room temperature to yield 2.3822 g (83%) of SBI-divinyl as a white solid. $^1$H NMR (500 MHz, $CDCl_3$) δ 7.34 (dd, J=7.9, 1.6 Hz, 2H), 7.17 (d, J=7.9 Hz, 2H), 6.85 (d, J=1.6 Hz, 2H), 6.64 (dd, J=17.6, 10.9 Hz, 2H), 5.62 (dd, J=17.6, 1.0 Hz, 2H), 5.12 (dd, J=10.9, 1.0 Hz, 2H), 2.32 (ABq, J=13.1 Hz, 4H), 1.42 (s, 6H), 1.36 (s, 6H).

Comparative Example 1

In a 40 mL vial, 0.9479 grams (7.28 mmoles) of divinylbenzene (DVB) (80 percent, technical grade) and 13.0 mg (79.2 micromoles) of azoisobutyronitrile (AIBN) was dissolved in 20.0 mL of EtOAc. The polymerization mixture thus consisted of an EtOAc solution of DVB at 5.0 weight percent solids and 1.4 weight percent AIBN (based on amount of DVB). The polymerization mixture was bubbled with nitrogen for 10 minutes. The vial was then capped and placed in a sand bath at 100° C. The polymerization was heated at this elevated temperature for 16 hours. A white precipitate had formed and was isolated by vacuum filtration and washed with EtOAc.

The solid was placed in a 40 mL vial and 20 mL of EtOAc was added to the vial. The vial was shaken on a wrist shaker for two hours at room temperature. The solid was again isolated by vacuum filtration and washed with EtOAc. The solid was placed in a 40 mL vial and 20 mL of EtOAc was added to the vial. The vial was shaken on a wrist shaker overnight. The solid was again isolated by vacuum filtration and washed with EtOAc. The solid was then dried under high vacuum at 90° C. overnight. This material had a BET calculated surface area ($SA_{BET}$) of 876.6 $m^2$/g and total pore volume of 0.821 $cm^3$/g (p/p°=0.948) as determined by nitrogen sorption.

Example 1

A 5.0 mg/mL solution of benzoyl peroxide (BPO) was made by dissolving 50.1 milligrams of BPO in 10 mL of EtOAc. In an 8 mL vial, 0.2000 grams (609 micromoles) of SBI-divinyl was dissolved in 1.80 mL of EtOAc. To this solution was added 800 microliters (μL) of the BPO/EtOAc solution. The polymerizable composition thus consisted of an EtOAc solution of SBI-divinyl at 7.9 weight percent solids and 2 weight percent BPO (based on amount of SBI-divinyl). The polymerizable composition was bubbled with nitrogen for 10 minutes. The vial was then capped and placed in a sand bath at 80° C. The polymerizable composition was heated at this elevated temperature for 17 hours. A white precipitate had formed and was isolated by vacuum filtration and washed with EtOAc.

The solid was placed in a 20 mL vial and 10 mL of EtOAc was added to the vial. The vial was shaken on a wrist shaker for one hour at room temperature. The solid was again isolated by vacuum filtration and washed with EtOAc. The solid was placed in a 20 mL vial and 10 mL of EtOAc was added to the vial. The solid was shaken on a wrist shaker overnight. The solid was again isolated by vacuum filtration and washed with EtOAc. The solid was then dried under high vacuum at 110° C. overnight. This material had a $SA_{BET}$ of 725.2 $m^2$/g and total pore volume of 0.471 $cm^3$/g (p/p°=0.949) as determined by nitrogen sorption.

Example 2

A 4.0 mg/mL solution of BPO was made by dissolving 40.0 milligrams of BPO in 10 mL of EtOAc. In a 20 mL vial, 0.2008 grams (611 micromoles) of SBI-divinyl was dissolved in 4.32 mL of EtOAc. To this solution was added 1.0 mL of the BPO/EtOAc solution. The polymerizable composition thus consisted of an EtOAc solution of SBI-divinyl at 4.0 weight percent solids and 2 weight percent BPO (based on amount of SBI-divinyl). The polymerizable composition was bubbled with nitrogen for 10 minutes. The vial was then capped and placed in a sand bath at 75° C. The polymerization was heated at this elevated temperature for 17 hours. A white precipitate had formed and was isolated by vacuum filtration and washed with EtOAc.

The solid was placed in a 20 mL vial and 10 mL of EtOAc was added to the vial. The vial was shaken on a wrist shaker for one hour at room temperature. The solid was again isolated by vacuum filtration and washed with EtOAc. The process of washing the solid by shaking in EtOAc was repeated two more times. The solid was then dried under high vacuum at 100° C. overnight. This material had a $SA_{BET}$ of 806.9 $m^2$/g and total pore volume of 0.562 $cm^3$/g (p/p°=0.950) as determined by nitrogen sorption.

Example 3

A 4.0 mg/mL solution of BPO was made by dissolving 40.0 milligrams of BPO in 10 mL of EtOAc. In a 20 mL vial, 0.2007 grams (611 micromoles) of SBI-divinyl was dissolved in 9.865 mL of EtOAc. To this solution was added 1.0 mL of the BPO/EtOAc solution. The polymerizable composition thus consisted of an EtOAc solution of SBI-divinyl at 2.0 weight percent solids and 2 weight percent BPO (based on amount of SBI-divinyl). The polymerizable composition was bubbled with nitrogen for 10 minutes. The vial was then capped and placed in a sand bath at 75° C. The polymerization was heated at this elevated temperature for 17 hours. A white precipitate had formed and was isolated by vacuum filtration and washed with EtOAc.

The solid was placed in a 20 mL vial and 10 mL of EtOAc was added to the vial. The vial was shaken on a wrist shaker for one hour at room temperature. The solid was again isolated by vacuum filtration and washed with EtOAc. The process of washing the solid by shaking in EtOAc was repeated two more times. The solid was then dried under high vacuum at 100° C. overnight. This material had a $SA_{BET}$ of 799.1 m²/g and total pore volume of 0.532 cm³/g (p/p°=0.950) as determined by nitrogen sorption.

Example 4

A 0.9 mg/mL solution of azoisobutyronitrile (AIBN) was made by dissolving 17.3 milligrams of AIBN in 19.2 mL of EtOAc. In a 20 mL vial, 0.3001 grams (914 micromoles) of SBI-divinyl was dissolved in 4.0 mL of EtOAc. To this solution was added 4.0 mL of the AIBN/EtOAc solution. The polymerizable composition thus consisted of an EtOAc solution of SBI-divinyl at 4.0 weight percent solids and 1.2 weight percent AIBN (based on amount of SBI-divinyl). The polymerizable composition was bubbled with nitrogen for 10 minutes. The vial was then capped and placed in a sand bath at 90° C. The polymerization was heated at this elevated temperature for 16 hours. A white precipitate had formed and was isolated by vacuum filtration and washed with EtOAc.

The solid was placed in a 20 mL vial and 10 mL of EtOAc was added to the vial. The vial was shaken on a wrist shaker for one hour at room temperature. The solid was again isolated by vacuum filtration and washed with EtOAc. The solid was placed in a 20 mL vial and 10 mL of EtOAc was added to the vial. The solid was shaken on a wrist shaker overnight. The solid was again isolated by vacuum filtration and washed with EtOAc. The solid was then dried under high vacuum at 90° C. overnight. This material had a $SA_{BET}$ of 808.8 m²/g and total pore volume of 0.533 cm³/g (p/p°=0.950) as determined by nitrogen sorption.

Example 5

A 0.9 mg/mL solution of AIBN was made by dissolving 17.3 milligrams of AIBN in 19.2 mL of EtOAc. In a 20 mL vial, 0.3002 grams (914 micromoles) of SBI-divinyl was dissolved in 6.0 mL of EtOAc. To this solution was added 2.0 mL of the AIBN/EtOAc solution. The polymerizable composition thus consisted of an EtOAc solution of SBI-divinyl at 4.0 weight percent solids and 0.6 weight percent AIBN (based on amount of SBI-divinyl). The polymerizable composition was bubbled with nitrogen for 10 minutes. The vial was then capped and placed in a sand bath at 90° C. The polymerization was heated at this elevated temperature for 16 hours. A white precipitate had formed and was isolated by vacuum filtration and washed with EtOAc.

The solid was placed in a 20 mL vial and 10 mL of EtOAc was added to the vial. The vial was shaken on a wrist shaker for one hour at room temperature. The solid was again isolated by vacuum filtration and washed with EtOAc. The solid was placed in a 20 mL vial and 10 mL of EtOAc was added to the vial. The solid was shaken on a wrist shaker overnight. The solid was again isolated by vacuum filtration and washed with EtOAc. The solid was then dried under high vacuum at 90° C. overnight. This material had a $SA_{BET}$ of 853.8 m²/g and total pore volume of 0.582 cm³/g (p/p°=0.950) as determined by nitrogen sorption.

FIG. 1 is the plot of the nitrogen adsorption and desorption isotherm at 77° K for Example 5. There is a rapid increase in adsorption at relative pressures up to 0.05. This isotherm is considered to be a Type I isotherm, which is characteristic for materials that contain micropores. That is, the pores are predominately microporous (i.e., the pore diameter is less than 2 nanometers). The desorption curve showed significant hysteresis, which is also characteristic of microporous materials.

Figure 2:
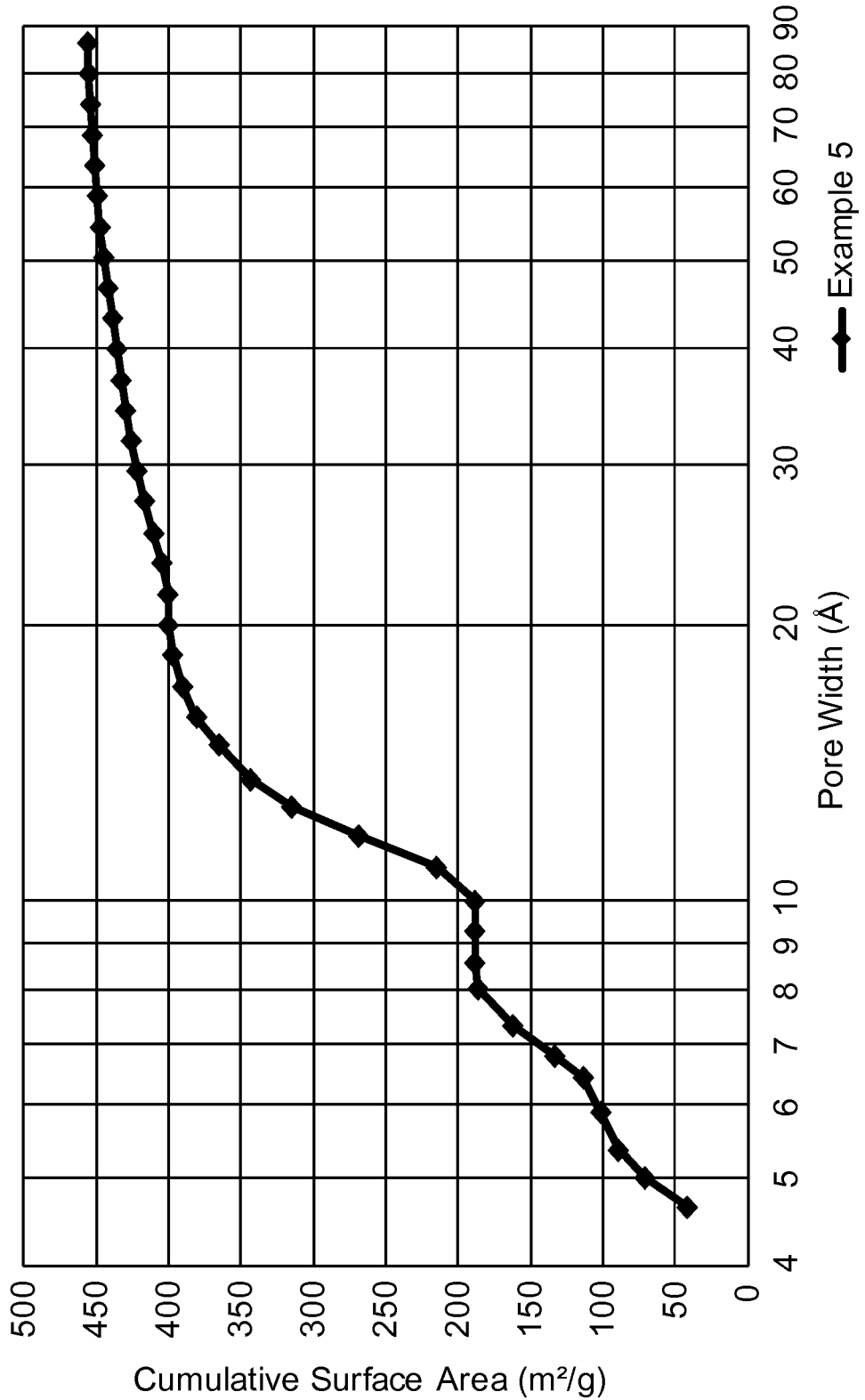
FIG. 2 is a plot of pore width (Angstroms) versus cumulative surface area for an exemplary porous polymeric material prepared from a monomer of Formula (I).

FIG. 2 is a plot of pore width (Angstroms) versus cumulative surface area for Example 5. This is based on analysis of the adsorption isotherm using the standard nitrogen DFT model, which tends to be most reliable for pores having a diameter up to about 9 nanometers. FIG. 2 suggests that the majority of the surface area is the result of pores having a diameter less than 20 Angstroms, which corresponds to micropores. The DFT model is described in the following book: P. A. Webb and C. Orr, *Surface Area and Pore Structure by Gas Adsorption: Analytical Methods in Fine Particle Technology*, Micromeritics Instrument Corporation, Norcross, Ga., pages 53-153 (1997).

Example 6

A 0.9 mg/mL solution of AIBN was made by dissolving 17.3 milligrams of AIBN in 19.2 mL of EtOAc. In a 20 mL vial, 0.3000 grams (913 micromoles) of SBI-divinyl was dissolved in 7.0 mL of EtOAc. To this solution was added 1.0 mL of the AIBN/EtOAc solution. The polymerizable composition thus consisted of an EtOAc solution of SBI-divinyl at 4.0 weight percent solids and 0.3 weight percent AIBN (based on amount of SBI-divinyl). The polymerizable composition was bubbled with nitrogen for 10 minutes. The vial was then capped and placed in a sand bath at 90° C. The polymerization was heated at this elevated temperature for 16 hours. A white precipitate had formed and was isolated by vacuum filtration and washed with EtOAc.

The solid was placed in a 20 mL vial and 10 mL of EtOAc was added to the vial. The vial was shaken on a wrist shaker for one hour at room temperature. The solid was again isolated by vacuum filtration and washed with EtOAc. The solid was placed in a 20 mL vial and 10 mL of EtOAc was added to the vial. The solid was shaken on a wrist shaker overnight. The solid was again isolated by vacuum filtration and washed with EtOAc. The solid was then dried under high vacuum at 90° C. overnight. This material had a $SA_{BET}$ of 832.6 m²/g and total pore volume of 0.562 cm³/g (p/p°=0.951) as determined by nitrogen sorption.

Example 7

A 1.4 mg/mL solution of dimethyl 2,2'-azobis(2-methylpropionate) (V-601) was made by dissolving 14.0 milligrams of V-601 in 10 mL of EtOAc. In a 20 mL vial, 0.2998 grams (913 micromoles) of SBI-divinyl was dissolved in 4.0 mL of EtOAc. To this solution was added 4.0 mL of the V-601/EtOAc solution. The polymerizable composition thus consisted of an EtOAc solution of SBI-divinyl at 4.0 weight percent solids and 1.9 weight percent V-601 (based on amount of SBI-divinyl). The polymerizable composition was bubbled with nitrogen for 10 minutes. The vial was then capped and placed in a sand bath at 90° C. The polymerization was heated at this elevated temperature for 16 hours. A white precipitate had formed and was isolated by vacuum filtration and washed with EtOAc.

The solid was placed in a 20 mL vial and 10 mL of EtOAc was added to the vial. The vial was shaken on a wrist shaker for two hours at room temperature. The solid was again isolated by vacuum filtration and washed with EtOAc. The solid was placed in a 20 mL vial and 10 mL of EtOAc was added to the vial. The solid was shaken on a wrist shaker for 72 hours. The solid was again isolated by vacuum filtration and washed with EtOAc. The solid was then dried under high vacuum at 90° C. overnight. This material had a $SA_{BET}$ of 817.8 m²/g and total pore volume of 0.577 cm³/g (p/p°=0.950) as determined by nitrogen sorption.

Example 8

A 1.4 mg/mL solution of V-601 was made by dissolving 14.0 milligrams of V-601 in 10 mL of EtOAc. In a 20 mL vial, 0.3002 grams (914 micromoles) of SBI-divinyl was dissolved in 6.0 mL of EtOAc. To this solution was added 2.0 mL of the V-601/EtOAc solution. The polymerizable composition thus consisted of an EtOAc solution of SBI-divinyl at 4.0 weight percent solids and 0.9 weight percent V-601 (based on amount of SBI-divinyl). The polymerizable composition was bubbled with nitrogen for 10 minutes. The vial was then capped and placed in a sand bath at 90° C. The polymerization was heated at this elevated temperature for 16 hours. A white precipitate had formed and was isolated by vacuum filtration and washed with EtOAc.

The solid was placed in a 20 mL vial and 10 mL of EtOAc was added to the vial. The vial was shaken on a wrist shaker for two hours at room temperature. The solid was again isolated by vacuum filtration and washed with EtOAc. The solid was placed in a 20 mL vial and 10 mL of EtOAc was added to the vial. The solid was shaken on a wrist shaker for 72 hours. The solid was again isolated by vacuum filtration and washed with EtOAc. The solid was then dried under high vacuum at 90° C. overnight. This material had a $SA_{BET}$ of 848.9 m$^2$/g and total pore volume of 0.613 cm$^3$/g (p/p°=0.951) as determined by nitrogen sorption.

Example 9

A 1.4 mg/mL solution of V-601 was made by dissolving 14.0 milligrams of V-601 in 10 mL of EtOAc. In a 20 mL vial, 0.3003 grams (914 micromoles) of SBI-divinyl was dissolved in 7.0 mL of EtOAc. To this solution was added 1.0 mL of the V-601/EtOAc solution. The polymerizable composition thus consisted of an EtOAc solution of SBI-divinyl at 4.0 weight percent solids and 0.5 weight percent V-601 (based on amount of SBI-divinyl). The polymerizable composition was bubbled with nitrogen for 10 minutes. The vial was then capped and placed in a sand bath at 90° C. The polymerization was heated at this elevated temperature for 16 hours. A white precipitate had formed and was isolated by vacuum filtration and washed with EtOAc.

The solid was placed in a 20 mL vial and 10 mL of EtOAc was added to the vial. The vial was shaken on a wrist shaker for two hours at room temperature. The solid was again isolated by vacuum filtration and washed with EtOAc. The solid was placed in a 20 mL vial and 10 mL of EtOAc was added to the vial. The solid was shaken on a wrist shaker for 72 hours. The solid was again isolated by vacuum filtration and washed with EtOAc. The solid was then dried under high vacuum at 90° C. overnight. This material had a $SA_{BET}$ of 824.8 m$^2$/g and total pore volume of 0.568 cm$^3$/g (p/p°=0.951) as determined by nitrogen sorption.

Example 10

A 5.0 mg/mL solution of BPO was made by dissolving 50.3 milligrams of BPO in 10 mL of methyl ethyl ketone (MEK). In an 8 mL vial, 0.2016 grams (614 micromoles) of SBI-divinyl was dissolved in 2.555 mL of MEK. To this solution was added 800 µL (microliter) of the BPO/MEK solution. The polymerizable composition thus consisted of an MEK solution of SBI-divinyl at 6.9% solids and 2.0 wt. % BPO (based on amount of SBI-divinyl). The polymerizable composition was bubbled with nitrogen for 10 minutes. The vial was then capped and placed in a sand bath at 80° C. The polymerization was heated at this elevated temperature for 18 hours. A white precipitate had formed and was isolated by vacuum filtration and washed with MEK.

The solid was placed in a 20 mL vial and 10 mL of MEK was added to the vial. The vial was shaken on a wrist shaker for four hours at room temperature. The solid was again isolated by vacuum filtration and washed with MEK. The solid was then dried under high vacuum at 90° C. overnight. This material had a $SA_{BET}$ of 408.6 m$^2$/g and total pore volume of 0.206 cm$^3$/g (p/p°=0.941) as determined by nitrogen sorption.

Example 11

A 5.0 mg/mL solution of BPO was made by dissolving 50.1 milligrams of BPO in 10 mL of EtOAc. In an 8 mL vial, 0.2000 grams (609 micromoles) of SBI-divinyl and 29 µL (203 micromoles) of DVB (80 percent, tech grade) was dissolved in 1.437 mL of EtOAc. To this solution was added 906 µL of the BPO/EtOAc solution. The polymerizable composition thus consisted of an EtOAc solution of SBI-divinyl/DVB in a 3:1 molar ratio at 9.6 weight percent solids and 2 weight percent BPO (based on amount of SBI-divinyl and DVB). The polymerizable composition was bubbled with nitrogen for 10 minutes. The vial was then capped and placed in a sand bath at 80° C. The polymerization was heated at this elevated temperature for 17 hours. A white precipitate had formed and was isolated by vacuum filtration and washed with EtOAc.

The solid was placed in a 20 mL vial and 10 mL of EtOAc was added to the vial. The vial was shaken on a wrist shaker for one hour at room temperature. The solid was again isolated by vacuum filtration and washed with EtOAc. The solid was placed in a 20 mL vial and 10 mL of EtOAc was added to the vial. The solid was shaken on a wrist shaker overnight. The solid was again isolated by vacuum filtration and washed with EtOAc. The solid was then dried under high vacuum at 110° C. overnight. This material had a $SA_{BET}$ of 739.7 m$^2$/g and total pore volume of 0.690 cm$^3$/g (p/p°=0.950) as determined by nitrogen sorption.

Example 12

A 5.0 mg/mL solution of BPO was made by dissolving 50.1 milligrams of BPO in 10 mL of EtOAc. In an 8 mL vial, 0.2000 grams (609 micromoles) of SBI-divinyl and 87 µL (609 micromoles) of DVB (80 percent, technical grade) was dissolved in 2.452 mL of EtOAc. To this solution was added 1.117 µL of the BPO/EtOAc solution. The polymerizable composition thus consisted of an EtOAc solution of SBI-divinyl/DVB in a 1:1 molar ratio at 8.0 weight percent solids and 2 weight percent BPO (based on amount of SBI-divinyl and DVB). The polymerizable composition was bubbled with nitrogen for 10 minutes. The vial was then capped and placed in a sand bath at 80° C. The polymerization was heated at this elevated temperature for 17 hours. A white precipitate had formed and was isolated by vacuum filtration and washed with EtOAc.

The solid was placed in a 20 mL vial and 10 mL of EtOAc was added to the vial. The vial was shaken on a wrist shaker for one hour at room temperature. The solid was again isolated by vacuum filtration and washed with EtOAc. The solid was placed in a 20 mL vial and 10 mL of EtOAc was added to the vial. The solid was shaken on a wrist shaker overnight. The solid was again isolated by vacuum filtration and washed with EtOAc. The solid was then dried under high vacuum at 110° C. overnight. This material had a $SA_{BET}$ of 810.1 m$^2$/g and total pore volume of 0.848 cm$^3$/g (p/p°=0.950) as determined by nitrogen sorption.

Example 13

A 5.0 mg/mL solution of BPO was made by dissolving 50.1 milligrams of BPO in 10 mL of EtOAc. In an 8 mL vial, 0.2003 grams (610 micromoles) of SBI-divinyl and 261 μL (1.83 mmoles) of DVB (80 percent, technical grade) was dissolved in 4.330 mL of EtOAc. To this solution was added 1.752 μL of the BPO/EtOAc solution. The polymerizable composition thus consisted of an EtOAc solution of SBI-divinyl/DVB in a 1:3 molar ratio at 7.4 weight percent solids and 2 weight percent BPO (based on amount of SBI-divinyl and DVB). The polymerizable composition was bubbled with nitrogen for 10 minutes. The vial was then capped and placed in a sand bath at 80° C. The polymerization was heated at this elevated temperature for 17 hours. A white precipitate had formed and was isolated by vacuum filtration and washed with EtOAc.

The solid was placed in a 20 mL vial and 10 mL of EtOAc was added to the vial. The vial was shaken on a wrist shaker for one hour at room temperature. The solid was again isolated by vacuum filtration and washed with EtOAc. The solid was placed in a 20 mL vial and 10 mL of EtOAc was added to the vial. The solid was shaken on a wrist shaker overnight. The solid was again isolated by vacuum filtration and washed with EtOAc. The solid was then dried under high vacuum at 110° C. overnight. This material had a $SA_{BET}$ of 840.5 m$^2$/g and total pore volume of 0.898 cm$^3$/g (p/p°=0.950) as determined by nitrogen sorption.

Figure 3:
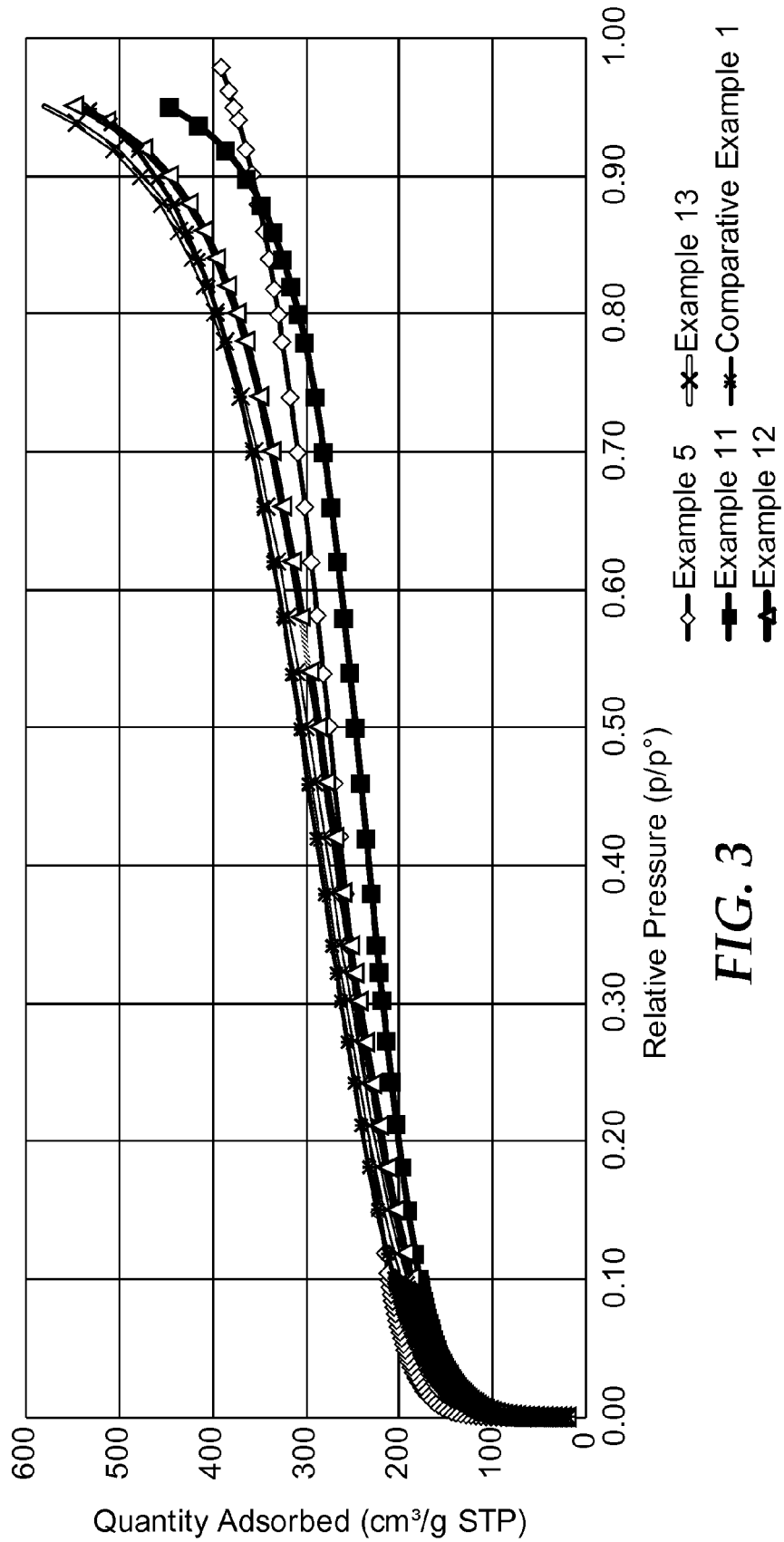
FIG. 3 is the plot of the nitrogen adsorption isotherms for several exemplary porous polymeric material (both a homopolymer and copolymers) prepared from a monomer of Formula (I) for a comparative example prepared from divinyl benzene.

FIG. 3 shows the nitrogen adsorption isotherms for Examples 5, 11, 12, and 13 plus Comparative Example 1. Example 5 was a homopolymer of a monomer of Formula (I) which was SBI-divinyl. Examples 11 to 13 were copolymers prepared using a monomer mixture of SBI-divinyl and technical grade DVB divinylbenzene. The molar ratio of SBI-divinyl to DVB was 3:1 in Example 11, 1:1 in Example 12, and 1:3 in Example 13. Comparative Example 1 was prepared using only technical grade DVB as the monomer. The technical grade of DVB contains about 20 weight percent ethyl styrene.

All samples shown in FIG. 3 have micropores as indicated by the rapid increase in the quantity adsorbed at relatively low relative pressures such as at relative pressures less than 0.05. The adsorption isotherm is relatively flat for Example 5 at relative pressures from about 0.2 to about 0.8. This flatness suggests that Example 5 contains relatively few mesopores. In contrast, Examples 11-13 and Comparative Example 1 have isotherms that are less flat in the region for a relative pressure of about 0.2 to about 0.8. This suggests that these samples contain more mesopores than Example 5. Additionally, the isotherms for Examples 11-13 and Comparative Example 1 tend to increase substantially above a relative pressure of about 0.8 while Example 5 is substantially flat. The increase above a relative pressure of about 0.8 suggests the presence of pores that are macropores. Stated differently, as the amount of DVB increases relative to the amount of SBI-divinyl, the percentage of the porosity attributable to micropores tends to decrease while the percentage of porosity attributable to mesopores or larger pores tends to increase.

Figure 4:
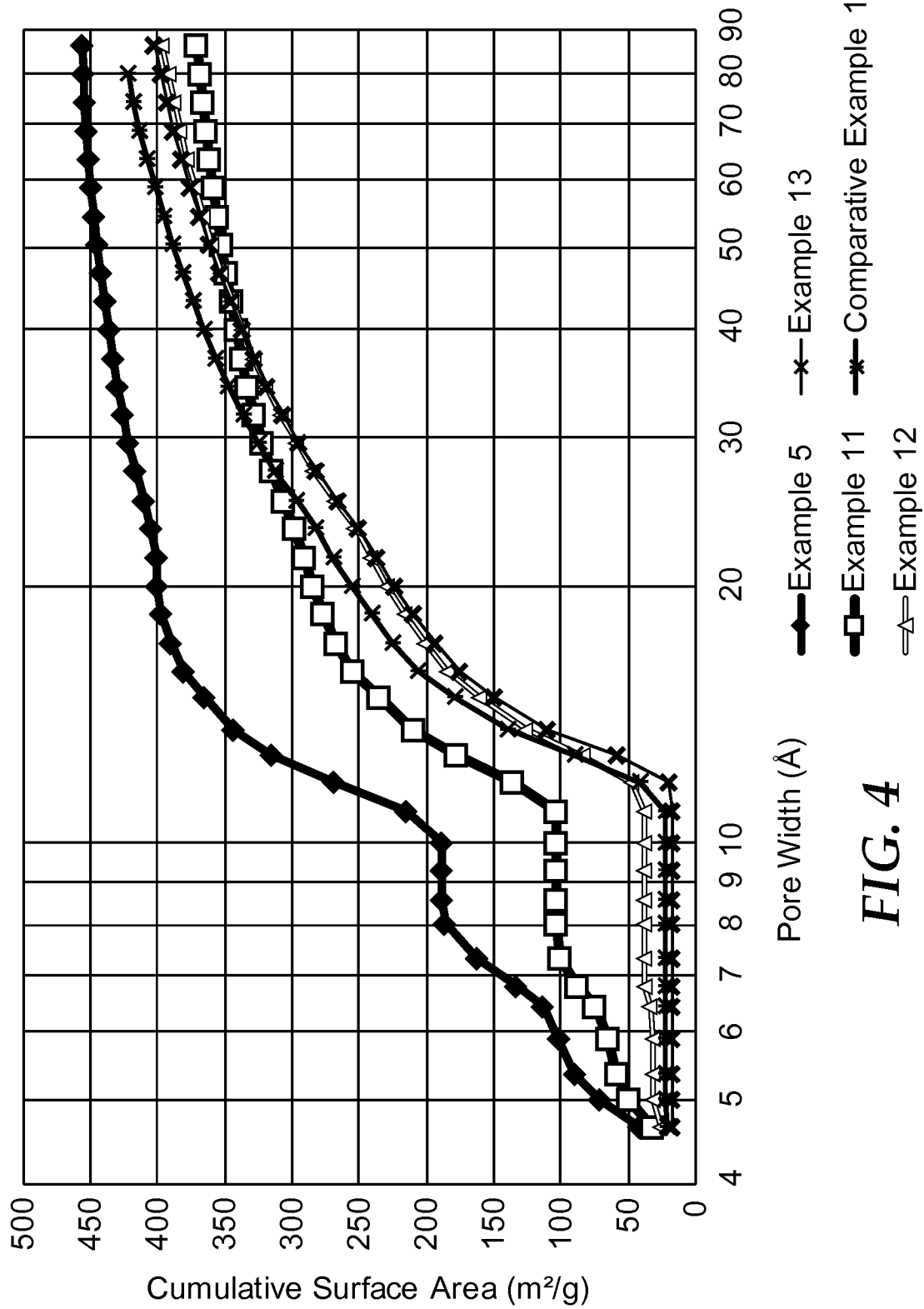
FIG. 4 is a plot of pore width (Angstroms) versus cumulative surface area for several exemplary porous polymeric material (both a homopolymer and copolymers) prepared from a monomer of Formula (I) and for a comparative example prepared from divinylbenzene.

FIG. 4 further supports this interpretation of the pore size distribution. This figure is a plot of pore width (Angstroms) versus cumulative surface area for Examples 5, Examples 11-13, and Comparative Example 5. The data is based on analysis of the adsorption isotherms using the standard nitrogen DFT model. The various plots suggest that Example 5 has the greatest surface area contribution from micropores. Example 12, Example 13, and Comparative Example 1 have much less microporosity. Larger pores contribute more to the total porosity for these samples.

I claim:
1. A compound of Formula (I)

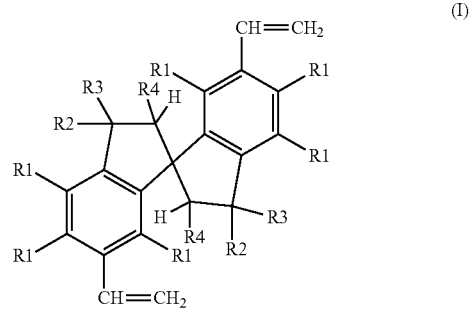

wherein
each R1 is independently hydrogen, halo, alkyl, aryl, alkaryl, or aralkyl;
each R2 is independently hydrogen, alkyl, alkoxy, aryl, alkaryl, aralkyl, hydroxyl, silyloxy, combines with a R3 connected to a same carbon atom to form a cyclic alkyl, combines with a R3 connected to the same carbon atom to form a cyclic alkyl that is fused to one or more carbocyclic rings, or combines with R3 and the carbon atom to which both R2 and R3 are connected to form a carbonyl group;
each R3 is independently hydrogen, alkyl, alkoxy, aryl, alkaryl, aralkyl, hydroxyl, silyloxy, combines with a R2 connected to a same carbon atom to form a cyclic alkyl, combines with a R2 connected to the same carbon atom to form a cyclic alkyl that is fused to one or more carbocyclic rings, combines with R2 and the carbon to which both R2 and R3 are connected to form a carbonyl group, or combines with R4 connected to adjacent carbon atom to form a carbon-carbon bond; and
each R4 is independently hydrogen or combines with R3 connected to an adjacent carbon atom to form a carbon-carbon bond.

2. The compound of claim 1, wherein each R1 is hydrogen or halo.

3. The compound of claim 1, wherein each R2 and each R3 are alkyl.

4. The compound of claim 1, wherein R4 is hydrogen.

5. The compound of claim 1, wherein the compound is 3,3,3',3'-tetramethyl-1,1'-spirobisindan-6,6'-divinyl.

6. A polymerizable composition comprising a compound of Formula (I)

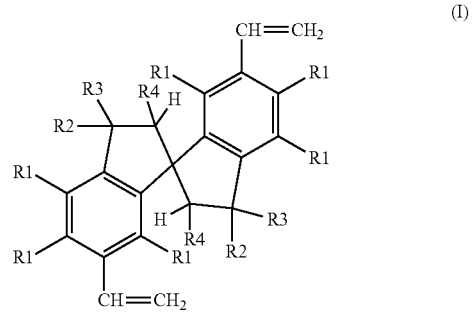

wherein
- each R1 is independently hydrogen, halo, alkyl, aryl, alkaryl, or aralkyl;
- each R2 is independently hydrogen, alkyl, alkoxy, aryl, alkaryl, aralkyl, hydroxyl, silyloxy, combines with a R3 connected to a same carbon atom to form a cyclic alkyl, combines with a R3 connected to the same carbon atom to form a cyclic alkyl that is fused to one or more carbocyclic rings, or combines with R3 and the carbon atom to which both R2 and R3 are connected to form a carbonyl group;
- each R3 is independently hydrogen, alkyl, alkoxy, aryl, alkaryl, aralkyl, hydroxyl, silyloxy, combines with a R2 connected to a same carbon atom to form a cyclic alkyl, combines with a R2 connected to the same carbon atom to form a cyclic alkyl that is fused to one or more carbocyclic rings, combines with R2 and the carbon to which both R2 and R3 are connected to form a carbonyl group, or combines with R4 connected to adjacent carbon atom to form a carbon-carbon bond; and
- each R4 is independently hydrogen or combines with R3 connected to an adjacent carbon atom to form a carbon-carbon bond.

7. The polymerizable composition of claim 6, wherein the polymerizable composition further comprises a polyvinyl aromatic monomer or a polyvinyl aromatic monomer substituted with one or more alkyl groups.

8. The polymerizable composition of claim 7, wherein the polyvinyl aromatic monomer is divinylbenzene, trivinylbenzene, divinylbenzene substituted with one or more alkyl groups, or trivinylbezene substituted with one or more alkyl groups.

9. The polymerizable composition of claim 6, further comprising up to 25 weight percent of a mono-vinyl aromatic monomer or a mono-vinyl aromatic monomer substituted with one or more alkyl groups.

10. The polymerizable composition of claim 9, wherein polymerizable composition comprises the 1 to 99 weight percent of a monomer of Formula (I), 0 to 25 weight percent of mono-vinyl aromatic monomer, and 1 to 99 weight percent of a polyvinyl aromatic monomer, wherein the weight percents are based on a total weight of monomers in the polymerizable composition.

11. A polymer comprising the polymerized product of a polymerizable composition comprising a compound of Formula (I)

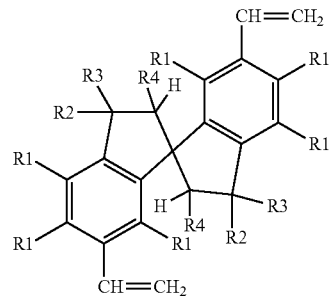

wherein
- each R1 is independently hydrogen, halo, alkyl, aryl, alkaryl, or aralkyl;
- each R2 is independently hydrogen, alkyl, alkoxy, aryl, alkaryl, aralkyl, hydroxyl, silyloxy, combines with a R3 connected to a same carbon atom to form a cyclic alkyl, combines with a R3 connected to the same carbon atom to form a cyclic alkyl that is fused to one or more carbocyclic rings, or combines with R3 and the carbon atom to which both R2 and R3 are connected to form a carbonyl group;
- each R3 is independently hydrogen, alkyl, alkoxy, aryl, alkaryl, aralkyl, hydroxyl, silyloxy, combines with a R2 connected to a same carbon atom to form a cyclic alkyl, combines with a R2 connected to the same carbon atom to form a cyclic alkyl that is fused to one or more carbocyclic rings, combines with R2 and the carbon to which both R2 and R3 are connected to form a carbonyl group, or combines with R4 connected to adjacent carbon atom to form a carbon-carbon bond; and
- each R4 is independently hydrogen or combines with R3 connected to an adjacent carbon atom to form a carbon-carbon bond.

12. The polymer of claim 11, wherein the polymerizable composition further comprises a polyvinyl aromatic monomer or a polyvinyl aromatic monomer substituted with one or more alkyl group.

13. The polymer of claim 11, wherein the polymer is porous.

14. The polymer of claim 13, wherein the polymer is microporous, mesoporous, or both.

15. The polymer of claim 11, wherein the BET surface area is at least 300 m²/gram.

\* \* \* \* \*